(12) United States Patent
Kimsey et al.

(10) Patent No.: US 11,426,171 B2
(45) Date of Patent: Aug. 30, 2022

(54) KNIFE FOR CIRCULAR SURGICAL STAPLER

(71) Applicant: Ethicon LLC, Guaynabo, PR (US)

(72) Inventors: John S. Kimsey, Walton, KY (US); Vijay K. Sakhare, Mason, OH (US)

(73) Assignee: Cilag GmbH International, Zug (CH)

(*) Notice: Subject to any disclaimer, the term of this patent is extended or adjusted under 35 U.S.C. 154(b) by 55 days.

(21) Appl. No.: 16/887,140

(22) Filed: May 29, 2020

(65) Prior Publication Data
US 2021/0369278 A1   Dec. 2, 2021

(51) Int. Cl.
*A61B 17/115* (2006.01)
*A61B 17/072* (2006.01)
*A61B 17/068* (2006.01)

(52) U.S. Cl.
CPC ...... *A61B 17/1155* (2013.01); *A61B 17/0686* (2013.01); *A61B 2017/07278* (2013.01); *A61B 2017/07285* (2013.01)

(58) Field of Classification Search
CPC ...... A61B 17/1155; A61B 2017/07278; A61B 17/115; A61B 17/072; A61B 2017/07285
See application file for complete search history.

(56) References Cited

U.S. PATENT DOCUMENTS

| | | | | |
|---|---|---|---|---|
| 4,289,133 A | * | 9/1981 | Rothfuss | A61B 17/115 227/175.3 |
| 4,573,468 A | * | 3/1986 | Conta | A61B 17/115 227/179.1 |
| 4,776,506 A | * | 10/1988 | Green | A61B 17/115 227/19 |
| 4,957,499 A | * | 9/1990 | Lipatov | A61B 17/115 227/180.1 |
| 5,205,459 A | * | 4/1993 | Brinkerhoff | A61B 17/115 227/179.1 |
| 5,271,543 A | * | 12/1993 | Grant | A61B 17/115 227/179.1 |
| 5,271,544 A | | 12/1993 | Fox et al. | |
| 5,275,322 A | | 1/1994 | Brinkerhoff et al. | |

(Continued)

FOREIGN PATENT DOCUMENTS

EP    2754398 A2    7/2014
WO    WO 2015/065484 A1    5/2015

OTHER PUBLICATIONS

U.S. Appl. No. 16/887,182 entitled, Shaft Attachment Feature for Circular Surgical Stapler filed May 29, 2020.

(Continued)

*Primary Examiner* — Gloria R Weeks
(74) *Attorney, Agent, or Firm* — Frost Brown Todd LLC

(57) ABSTRACT

An apparatus includes a body, a shaft, and a stapling head assembly. The shaft extends distally from the body. The stapling head assembly is positioned at a distal end of the shaft. The stapling head assembly includes a staple driver member and a knife member. The staple driver member is configured to drive a plurality of staples into tissue. The knife member is configured to cut through the tissue. The knife member includes a proximal end, a distal end, and a cylindrical body extending between the proximal and distal ends. The cylindrical body includes at least one coupling feature that operatively couples the knife member with the staple driver member.

20 Claims, 24 Drawing Sheets

(56) References Cited

U.S. PATENT DOCUMENTS

| | | | |
|---|---|---|---|
| 5,285,945 A | 2/1994 | Brinkerhoff et al. | |
| 5,292,053 A | 3/1994 | Bilotti et al. | |
| 5,333,773 A * | 8/1994 | Main | A61B 17/115 227/179.1 |
| 5,350,104 A * | 9/1994 | Main | A61B 17/115 227/179.1 |
| 5,533,661 A | 7/1996 | Main et al. | |
| 5,588,579 A * | 12/1996 | Schnut | A61B 17/115 227/175.1 |
| 6,050,472 A | 4/2000 | Shibata | |
| 6,193,129 B1 * | 2/2001 | Bittner | A61B 17/1114 227/180.1 |
| 7,168,604 B2 * | 1/2007 | Milliman | A61B 17/1114 227/175.1 |
| 7,364,060 B2 * | 4/2008 | Milliman | A61B 17/068 227/175.1 |
| 7,770,776 B2 * | 8/2010 | Chen | A61B 17/115 227/180.1 |
| 7,918,377 B2 * | 4/2011 | Measamer | A61B 17/1155 227/180.1 |
| 7,967,181 B2 * | 6/2011 | Viola | A61B 17/115 227/180.1 |
| 8,567,655 B2 * | 10/2013 | Nalagatla | A61B 17/1114 227/175.1 |
| 8,573,464 B2 * | 11/2013 | Nalagatla | A61B 17/1155 227/179.1 |
| 8,910,847 B2 * | 12/2014 | Nalagatla | H04B 7/0682 227/179.1 |
| 9,161,803 B2 * | 10/2015 | Yates | A61B 18/1445 |
| 9,421,013 B2 * | 8/2016 | Patel | A61B 17/068 |
| 9,681,871 B2 * | 6/2017 | Williams | A61B 17/068 |
| 9,713,469 B2 * | 7/2017 | Leimbach | A61B 17/1155 |
| 9,730,694 B2 * | 8/2017 | Scirica | A61B 17/0682 |
| 9,861,368 B2 * | 1/2018 | Racenet | A61B 17/07207 |
| 9,907,552 B2 * | 3/2018 | Measamer | A61B 17/1155 |
| 9,936,949 B2 * | 4/2018 | Measamer | A61B 17/068 |
| 10,092,292 B2 * | 10/2018 | Boudreaux | A61B 17/07207 |
| 10,226,253 B2 * | 3/2019 | DiNardo | A61B 17/068 |
| 10,405,864 B2 * | 9/2019 | Zhan | A61B 17/1155 |
| 10,478,189 B2 * | 11/2019 | Bear | H02J 7/00 |
| 2011/0278346 A1 * | 11/2011 | Hull | A61B 17/1155 227/180.1 |
| 2013/0060258 A1 * | 3/2013 | Giacomantonio | A61B 17/1114 606/110 |
| 2013/0181035 A1 * | 7/2013 | Milliman | A61B 17/068 227/180.1 |
| 2015/0083772 A1 * | 3/2015 | Miller | A61B 17/1155 227/175.1 |
| 2015/0173757 A1 * | 6/2015 | Williams | A61B 17/072 227/180.1 |
| 2016/0157856 A1 * | 6/2016 | Williams | A61B 17/068 227/175.1 |
| 2017/0258471 A1 * | 9/2017 | DiNardo | A61B 17/1155 |
| 2018/0132849 A1 * | 5/2018 | Miller | A61B 17/07207 |
| 2018/0132853 A1 * | 5/2018 | Miller | A61B 17/1155 |
| 2018/0233850 A1 * | 8/2018 | Penna | A61B 17/1155 |
| 2018/0310938 A1 * | 11/2018 | Kluener | A61B 17/1155 |
| 2020/0138441 A1 * | 5/2020 | Sgroi, Jr. | A61B 17/1155 |
| 2020/0281596 A1 * | 9/2020 | Wise | A61B 17/1114 |

OTHER PUBLICATIONS

International Search Report and Written Opinion dated Aug. 25, 2021, for International Application No. PCT/EP2021/064388, 18 pages.

* cited by examiner

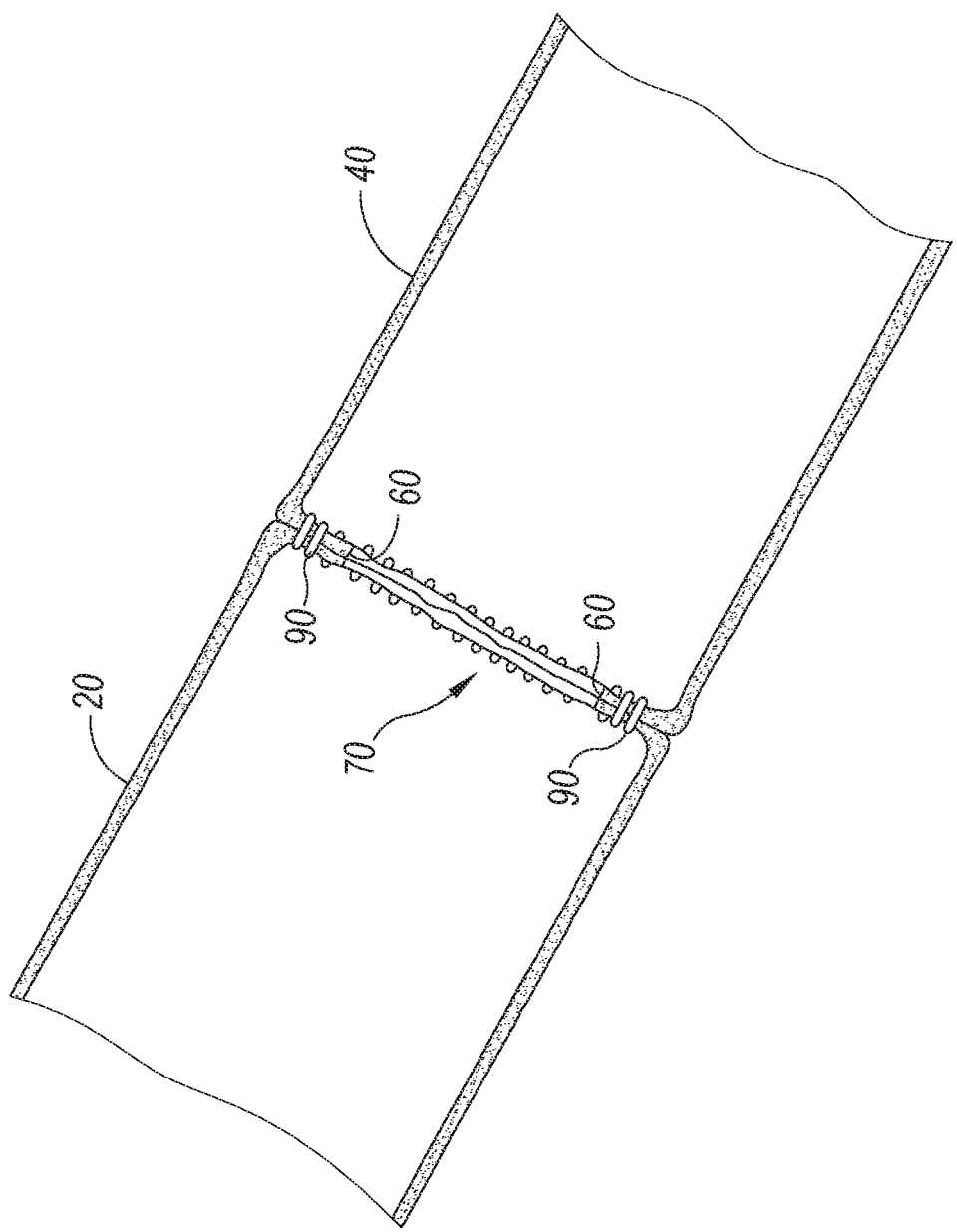

KNIFE FOR CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; and U.S. Pat. No. 9,713,469, entitled "Surgical Stapler with Rotary Cam Drive," issued Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 13E depicts a cross-sectional side view of the first and second sections of the digestive tract of FIG. 13A joined together at an end-to-end anastomosis;

Figure 1:
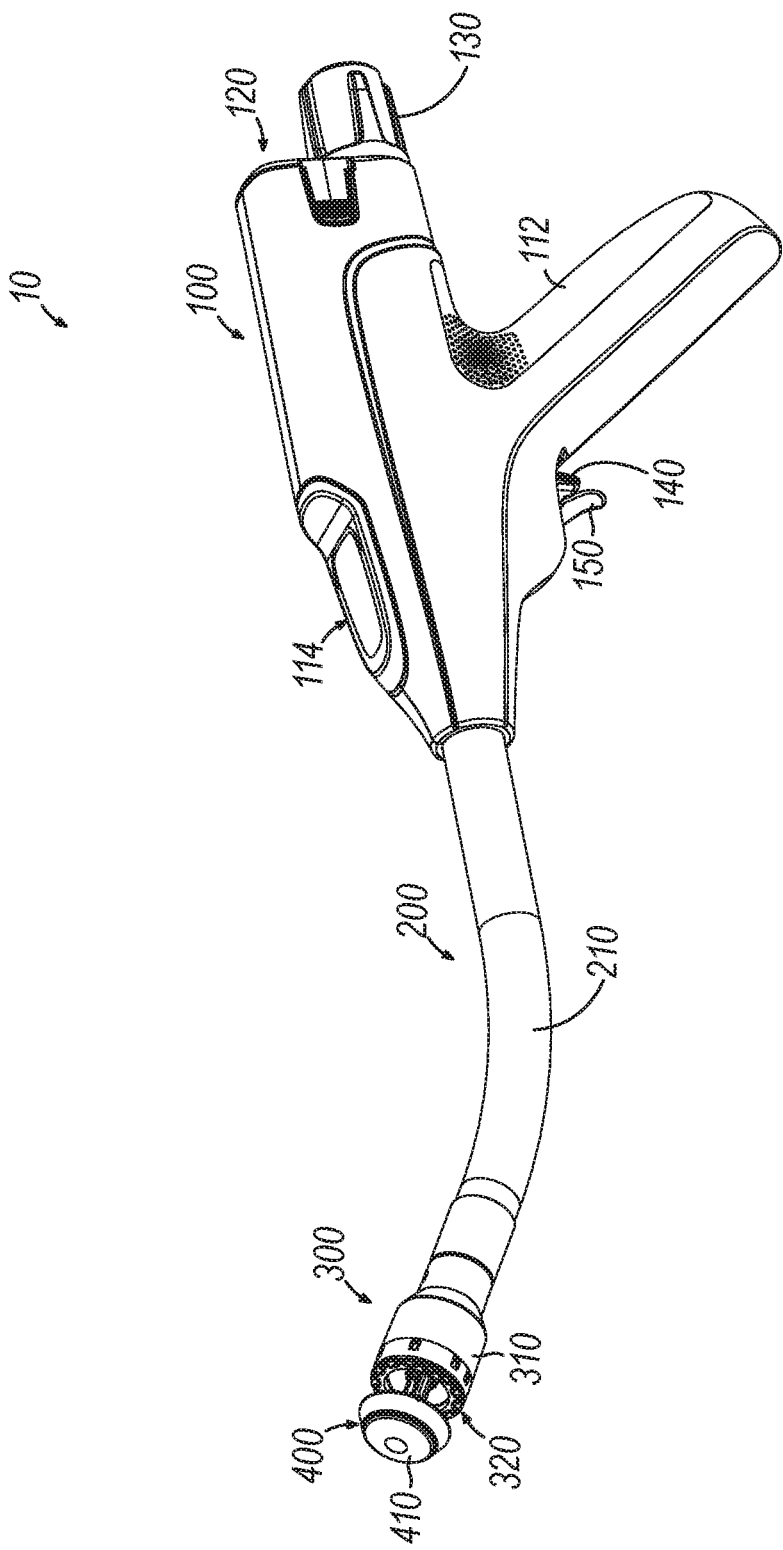
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

This application incorporates by reference the disclosures of U.S. Pub. No. 2015/0083772, entitled "Surgical Stapler with Rotary Cam Drive and Return," published on Mar. 26, 2015, now abandoned; U.S. Pat. No. 9,907,552, entitled "Control Features for Motorized Surgical Stapling Instrument," issued on Mar. 6, 2018; U.S. Pat. No. 10,478,189, entitled "Method of Applying an Annular Array of Staples to Tissue," issued on Nov. 19, 2019; U.S. Pub. No. 2018/0132853, entitled "Circular Stapler with Recessed Deck," published May 17, 2018, issued as U.S. Pat. No. 10,980,542 on Apr. 20, 2021; U.S. Pub. No. 2018/0132849, entitled "Staple Forming Pocket Configurations for Circular Surgical Stapler Anvil," published May 17, 2018, now abandoned; U.S. Pub. No. 2018/0310938, entitled "Hysteresis Removal Feature in Surgical Stapling Instrument," published Nov. 1, 2018, issued as U.S. Pat. No. 10,695,068 on Jun. 30, 2020.

I. Overview of Exemplary Circular Stapling Surgical Instrument

Figure 2:
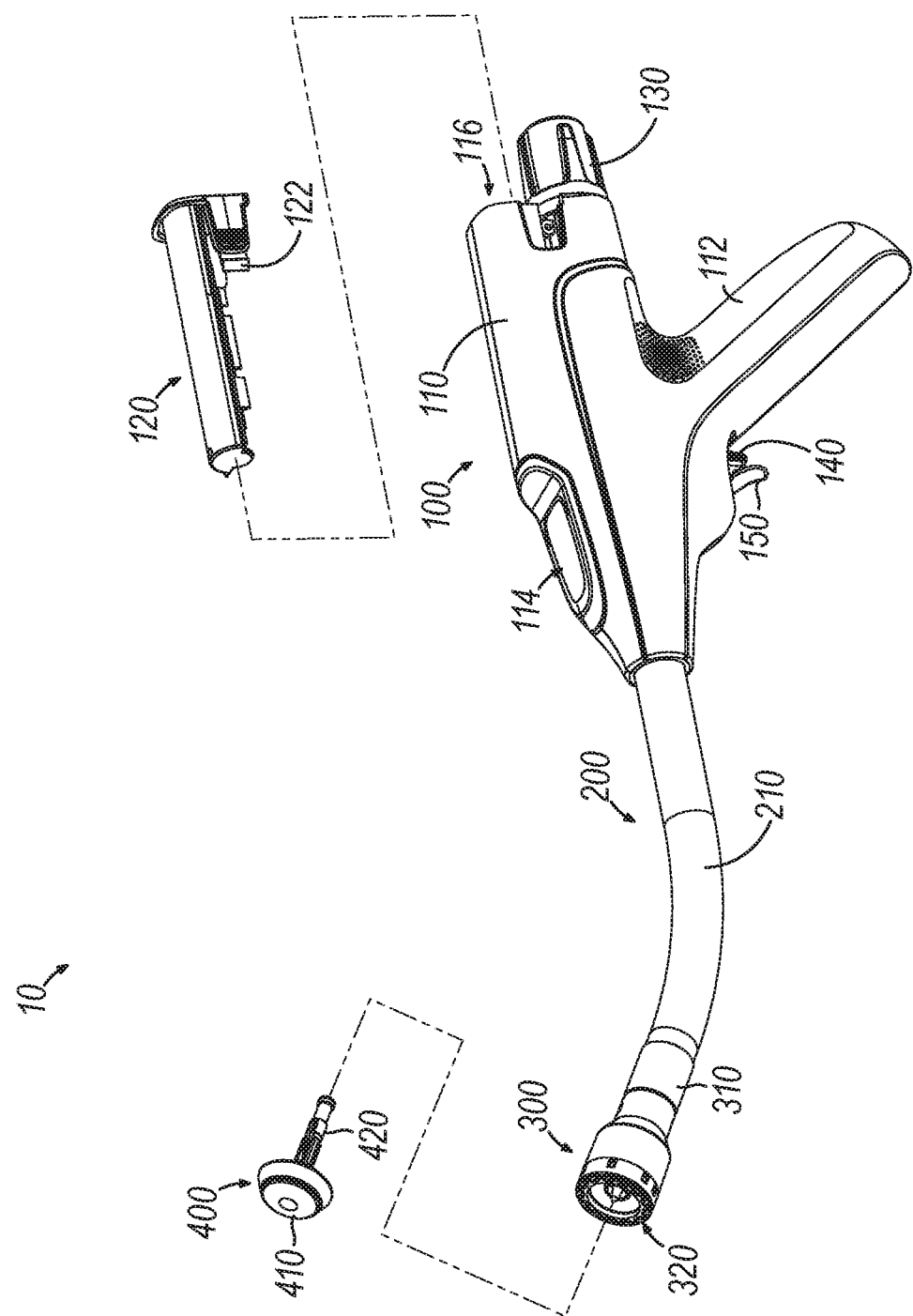
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end, side-to-side, or end-to-side anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (100) further includes a user feedback feature (114). In some versions, a series of hash marks, colored regions, and/or other fixed indicators are positioned adjacent to user feedback feature (114). Various suitable alternative features and configurations for handle assembly (100) will be apparent to those of ordinary skill in the art in view of the teachings herein.

Instrument (10) of the present example further includes a battery pack (120). Battery pack (120) is operable to provide electrical power to a motor (not shown) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery pack (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

II. Exemplary Drive Assembly

Figure 3:
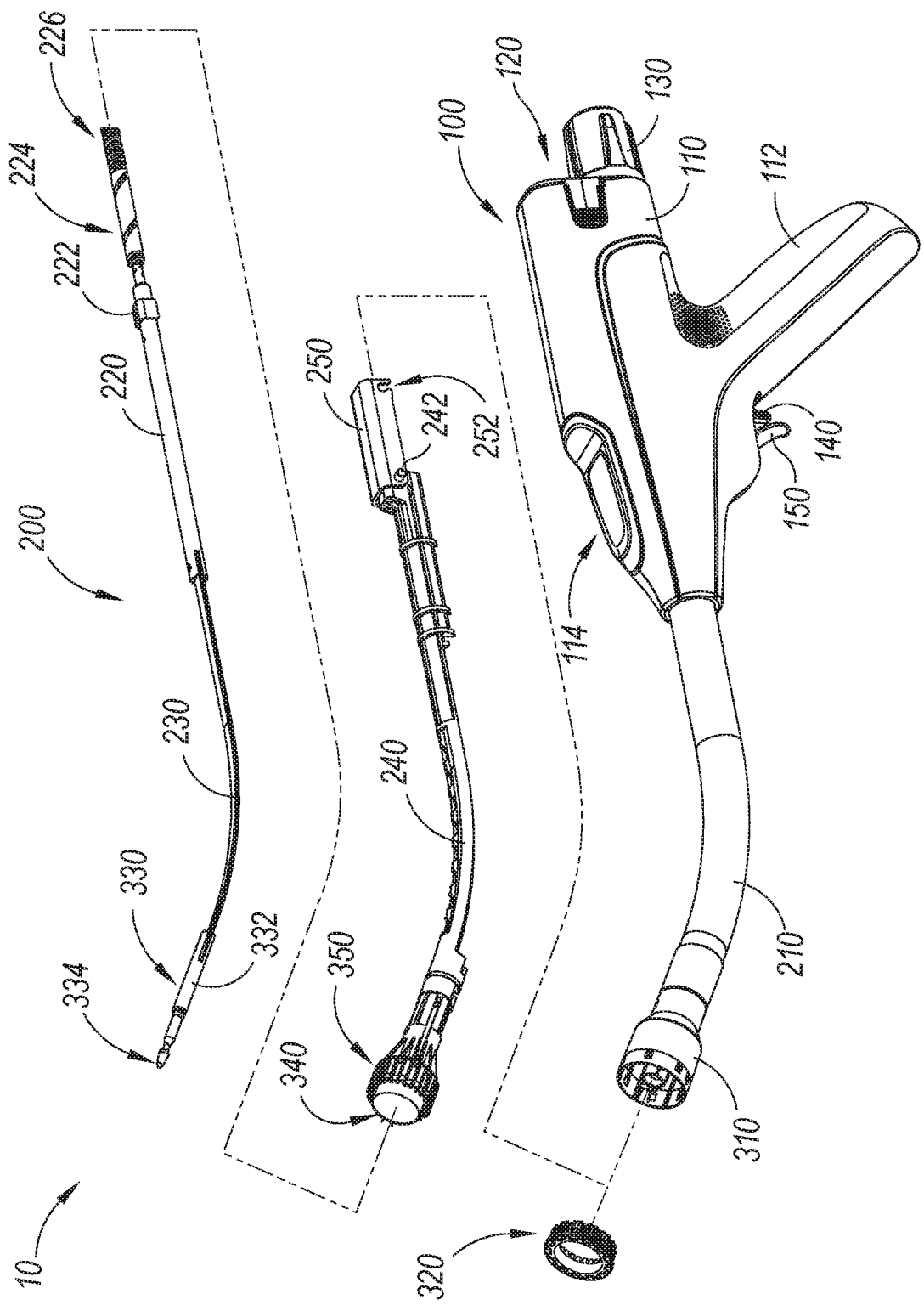
FIG. 3 depicts an exploded perspective view of the circular stapler of FIG. 1, with portions of a shaft assembly shown separately from each other.

FIG. 3 shows various components of shaft assembly (200), which couples components of stapling head assembly (300) with components of handle assembly (100). In particular, and as noted above, shaft assembly (200) includes an outer sheath (210) that extends between handle assembly (100) and a body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of a shaft (332) of a trocar (330). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to shaft (332) of trocar (330). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Drive bracket (250) includes notches (252).

While not shown in FIG. 3, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

As shown in FIG. 3, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, firing trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

III. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 4:
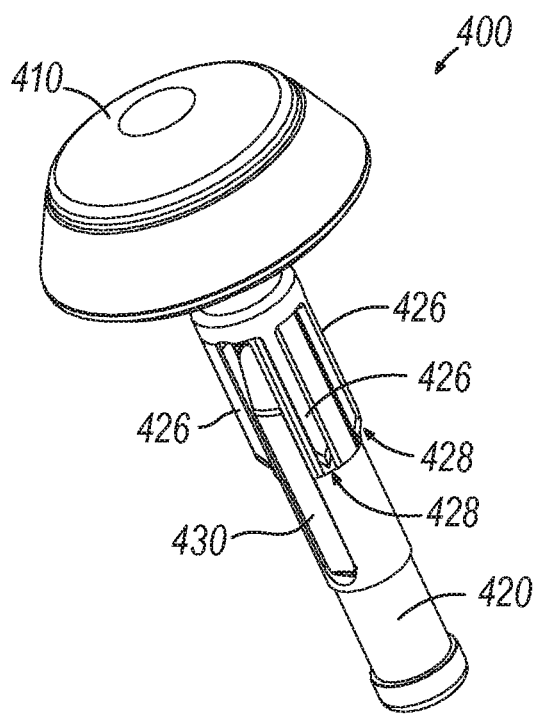
FIG. 4 depicts a perspective view of the anvil of the circular stapler of FIG. 1.
Figure 5:
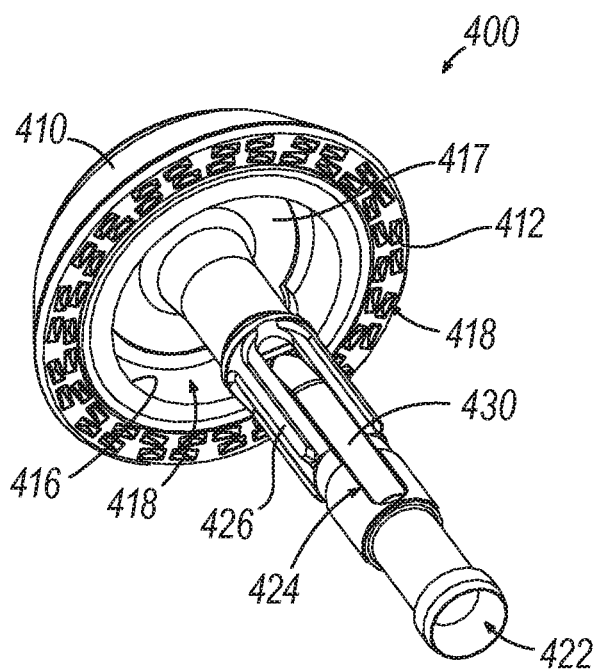
FIG. 5 depicts another perspective view of the anvil of FIG. 4.
Figure 6:
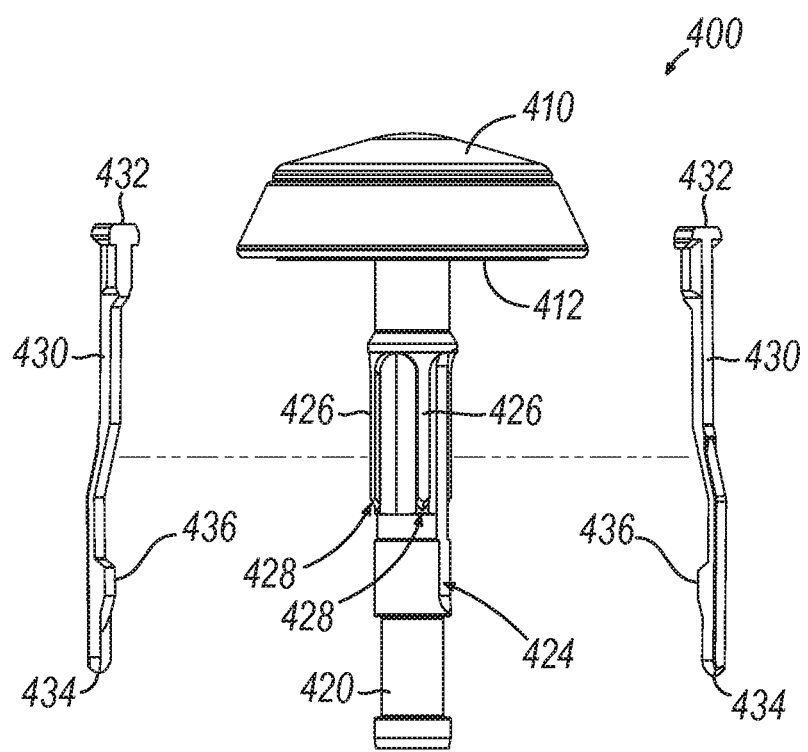
FIG. 6 depicts an exploded side elevational view of the anvil of FIG. 4.

As best seen in FIGS. 4-6, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 4, each latch member (430) includes a "T" shaped distal end (432), a rounded proximal end (434), and a latch shelf (436) located distal to proximal end (434). "T"

shaped distal ends (432) secure latch members (430) within bore (422). Latch members (430) are positioned within bore (422) such that proximal ends (434) are positioned at the proximal ends of lateral openings (424), which are formed through the sidewall of shank (420). Lateral openings (424) thus provide clearance for proximal ends (434) and latch shelves (436) to deflect radially outwardly from the longitudinal axis defined by shank (420). However, latch members (430) are configured to resiliently bias proximal ends (434) and latch shelves (436) to pivot radially inwardly toward the longitudinal axis defined by shank (420). Latch members (430) thus act as retaining clips. This allows anvil (400) to be removably secured to trocar (330) of stapling head assembly (300) as will be described in greater detail below. It should be understood, however, that latch shelves (436) are merely optional. Anvil (400) may be removably secured to trocar (330) using any other suitable components, features, or techniques.

As best seen in FIGS. 4-5, shank (420) of the present example includes a set of longitudinally extending splines (426) that are spaced about shank (420) in an angular array. The proximal end of each spline (426) includes a respective lead-in edge (428). A plurality of longitudinally extending splines (316) (see FIG. 8) are equidistantly spaced in an angular array within bore (314). As described in greater detail below, splines (426) are configured to engage corresponding splines (316) of body member (310) of stapling head assembly (300) in order to consistently provide a predetermined angular alignment between anvil (400) and stapling head assembly (300). As also described below, this angular alignment may ensure that staple forming pockets (414) of anvil (400) are consistently angularly aligned appropriately with staple openings (324) of stapling head assembly (300).

In some instances, it may be desirable to change the configuration and arrangement of staple forming pockets (414) in anvil (400). It should be understood that reconfiguring and rearranging staple forming pockets (414) may result in reconfiguration and rearrangement of staples (90) that are formed by staple forming pockets (414). For instance, the configuration and arrangement of staple forming pockets (414) may affect the structural integrity of an anastomosis (70) that is secured by staples (90). In addition, the configuration and arrangement of staple forming pockets (414) may affect the hemostasis that is achieved at an anastomosis (70) that is secured by staples (90). The following description relates to several exemplary variations of anvil (400), providing staple forming pocket configurations and arrangements that differ from those of staple forming pockets (414). Various suitable ways in which the alternatives to anvil (400) described below may be incorporated into instrument (10) will be apparent to those of ordinary skill in the art in view of the teachings herein.

For example, the staples formed using an exemplary alternative anvil may have an appearance similar to at least some of the staples shown and described in U.S. Pat. No. 10,092,292, entitled "Staple Forming Features for Surgical Stapling Instrument," issued Oct. 9, 2018, the disclosure of which is incorporated by reference herein. By way of further example only, the staples formed may have an appearance similar to at least some of the staples shown and described in U.S. Pub. No. 2018/0132849, entitled "Staple Forming Pocket Configurations for Circular Surgical Stapler Anvil," published May 17, 2018, now abandoned, the disclosure of which is incorporated by reference herein.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

IV. Exemplary Stapling Head Assembly

A. Overview

Figure 7:
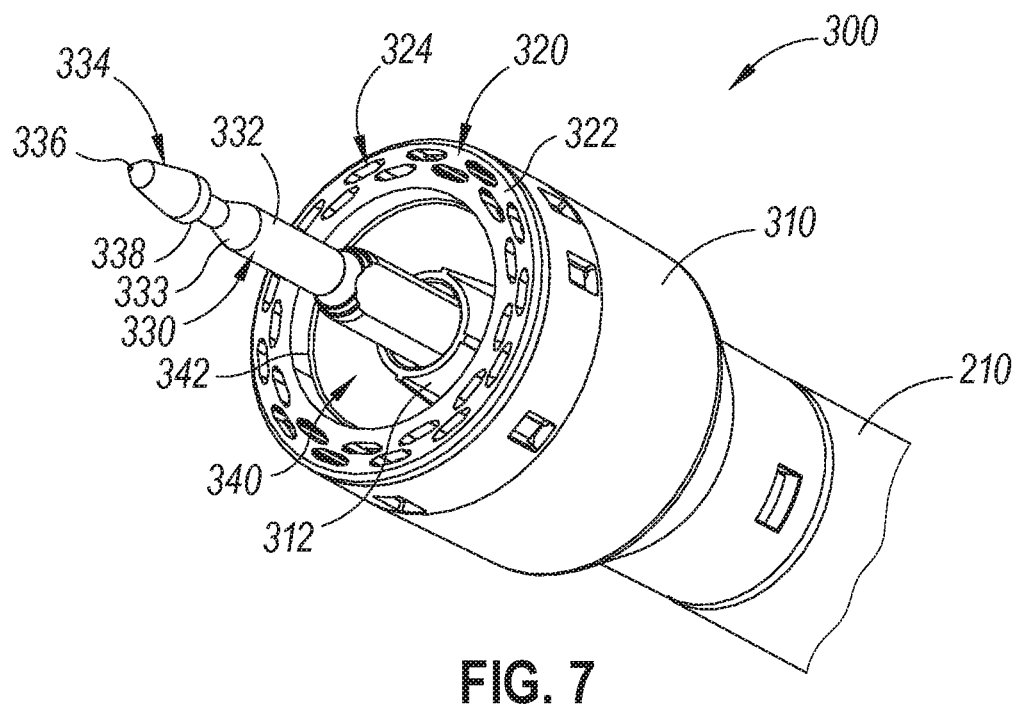
FIG. 7 depicts a perspective view of a stapling head assembly of the circular stapler of FIG. 1.
Figure 8:
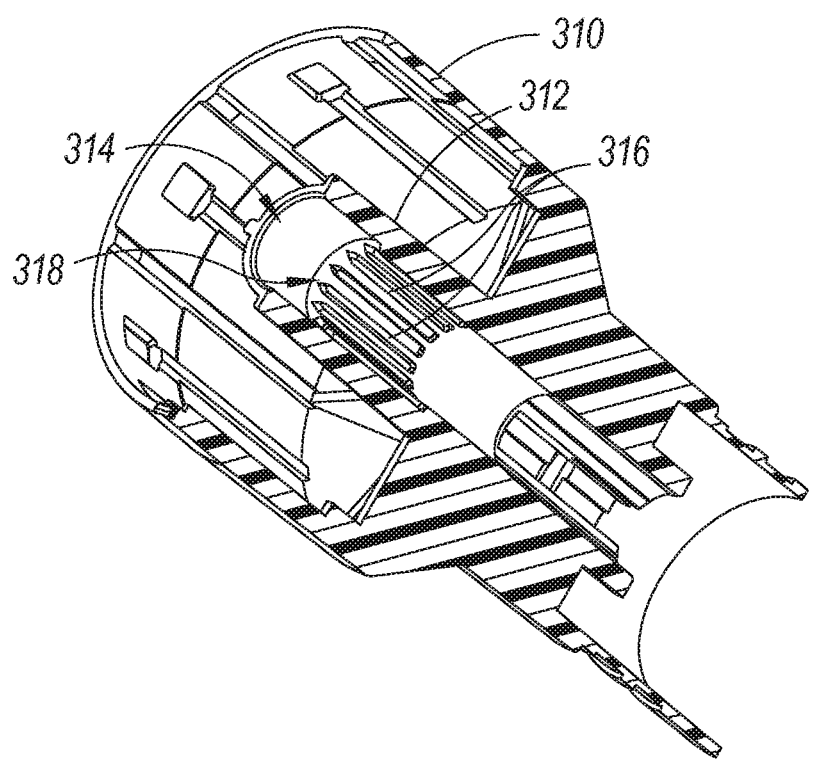
FIG. 8 depicts a perspective cross-sectional view of an inner body member of the stapling head assembly of FIG. 7.
Figure 9:
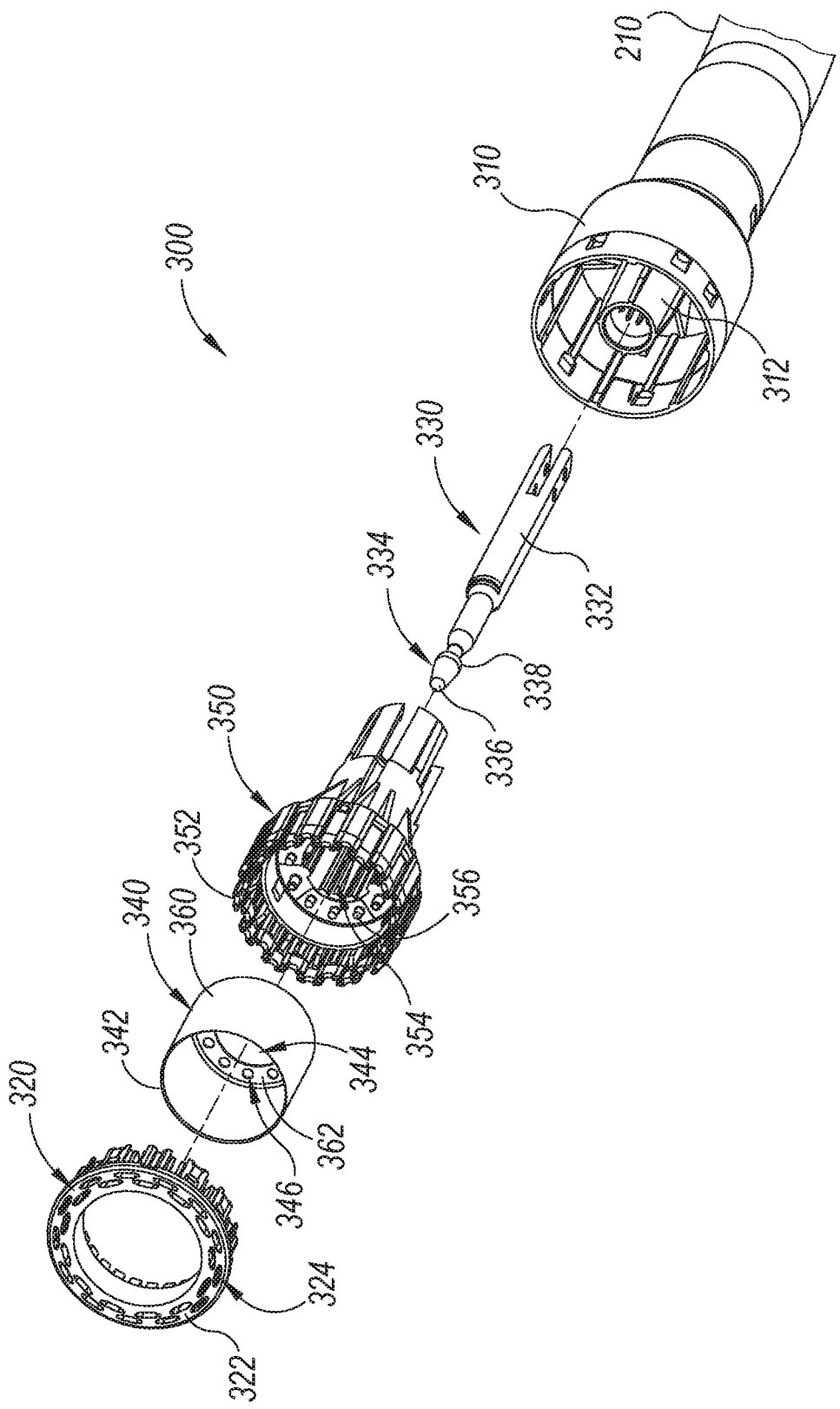
FIG. 9 depicts an exploded perspective view of the stapling head assembly of FIG. 7.

As best seen in FIGS. 7-9, stapling head assembly (300) of the present example is coupled to a distal end of shaft assembly (200) and comprises body member (310) and a slidable staple driver member (350). Body member (310) includes a distally extending cylindraceous inner core member (312). Body member (310) is fixedly secured to an outer sheath (210) of shaft assembly (200). Body member (310) and outer sheath (210) thus serve together as a mechanical ground for stapling head assembly (300).

As shown in FIG. 8, inner core member (312) of body member (310) defines a bore (314). When shank (420) is secured to trocar (330) and trocar (330) is retracted proximally, the inner diameter of bore (314) in inner core member (312) of body member (310) laterally constrains latch members (430) to maintain engagement between latch shelves (436) and proximal surface (338) of a head (334) of trocar (330). This engagement prevents anvil (400) from being released from trocar (330) during firing of stapling head assembly (300). The distal ends of splines (316) include lead-in edges (318) that are configured to complement lead-in edges (428) of splines (426) on shank (420) of anvil (400). In particular, after shank (420) is secured to trocar (330) as described in greater detail below, and as anvil (400) is thereafter retracted proximally relative to stapling head assembly (300) as also described in greater detail below, lead-in edges (318, 428) may cooperatively engage each other to drive anvil (400) to rotate relative to trocar (330) to angularly align splines (426) of anvil (400) with the gaps between splines (316) of body member (310). Thus, splines (316, 426) are configured to cooperate with each other to ensure that staples ejected through staple openings (324) are accurately driven into corresponding staple forming pockets (414) on a consistent basis, regardless of the angular orientation of anvil (400) relative to stapling head assembly (300) at the time anvil (400) is initially secured to trocar (330).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and head (334). Head (334) includes a pointed tip (336) and an inwardly extending proximal surface (338). Shaft (332) thus provides a reduced outer diameter just proximal to head (334), with proximal surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within body member (310) in response to activation of the motor as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive inner core member (312) of body member (310). An annular array of studs (356) project distally from a distally presented surface surrounding bore (354).

A knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) has a cylindrical wall (360) integrally together formed with a proximal flange (362). Proximal flange (362) extends radially inwardly relative to cylindrical wall (360). An inner diameter of proximal flange (362) of knife member (340) defines an opening (344) that is configured to coaxially receive an inner core member (e.g., inner core member (312) of body member (310)). Proximal flange (362) includes an annular array of openings (346). Annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and staple driver member (350) will be apparent to those of ordinary skill in the art in view of the teachings herein.

A deck member (320) is fixedly secured to body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should also be understood that, in some instances, the configuration and arrangement of staple openings (324) in deck member (320) may be modified just like the arrangement of staple forming pockets (414). It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein. As best seen in FIG. 7, deck member (320) defines an inner diameter that is just slightly larger than the outer diameter defined by knife member (340). Deck member (320) is thus configured to allow knife member (340) to translate distally to a point where cutting edge (342) is distal to deck surface (322).

B. Exemplary Alternative Knife Member and Staple Driver Member

Figure 10:
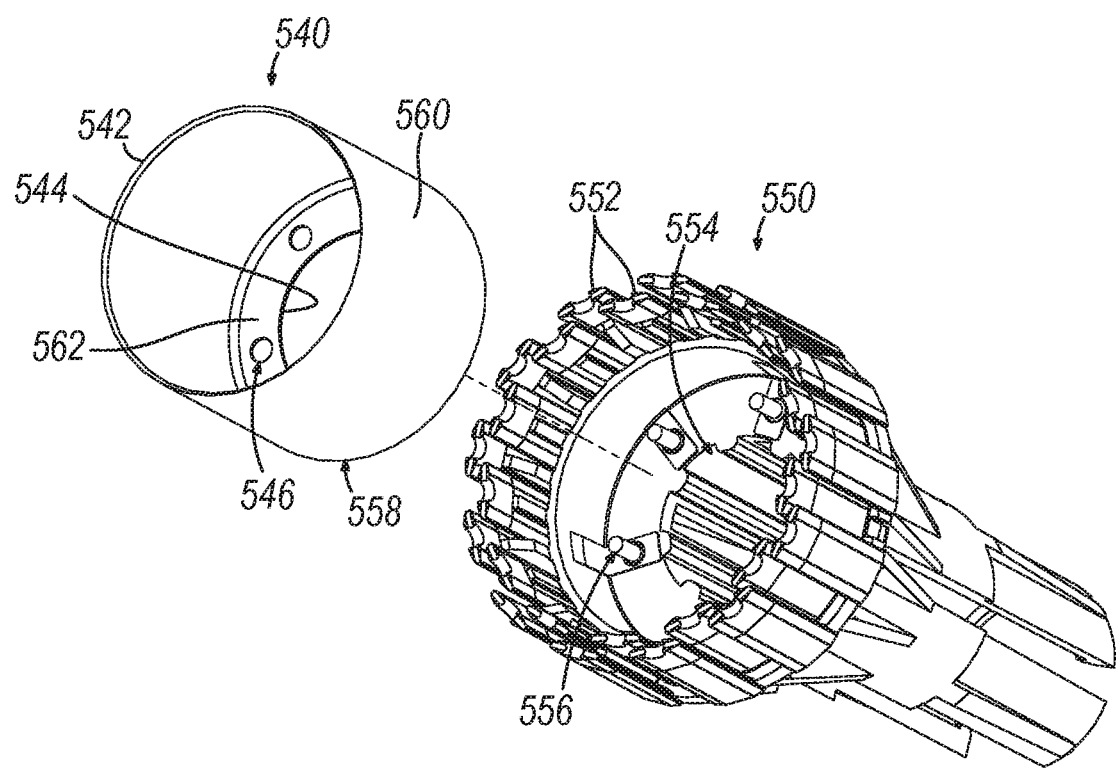
FIG. 10 depicts an exploded perspective view of a first exemplary alternative knife member and a first exemplary alternative staple driver member that may be incorporated into the stapling head assembly of FIG. 7.
Figure 11:
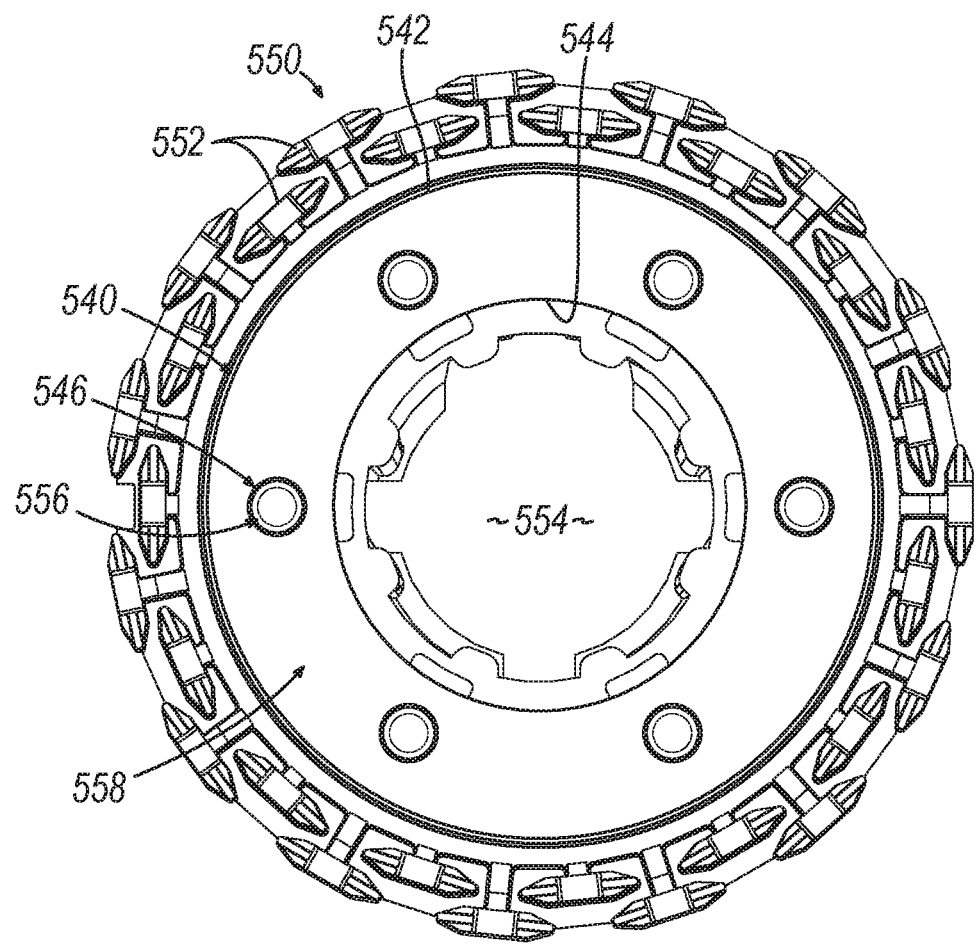
FIG. 11 depicts a top plan view of the knife member and the staple driver member of FIG. 10.

FIGS. 10-11 show a first exemplary alternative knife member (540) and a first exemplary alternative staple driver member (550) that may be used with a modified version of instrument (10). Particularly, FIG. 10 shows an exploded perspective view of knife member (540) and staple driver member (550), and FIG. 11 shows a top plan view of knife member (540) and staple driver member (550) of FIG. 10. Knife member (540) and staple driver member (550) of this example are configured and operable like knife member (340) and staple driver member (350) described in detail above, except for the differences described below.

Similar to staple driver member (350), staple driver member (550) is operable to actuate longitudinally within a body member (e.g., body member (310)) in response to activation of the motor. Staple driver member (550) includes two distally presented concentric annular arrays of staple drivers (552). Staple drivers (552) are arranged to correspond with the arrangement of staple forming pockets (similar to staple forming pockets (414)) described above. Staple driver member (550) defines a bore (554) that is configured to coaxially receive an inner core member (e.g., inner core member (312) of body member (310)). An annular array of studs (556) project distally from a distally presented surface surrounding bore (554).

Similar to knife member (340), knife member (540) may be coaxially positioned within staple driver member (550). Knife member (540) includes a distally presented, sharp circular cutting edge (542). Knife member (540) includes a body (558). Body (558) has a cylindrical wall (560) integrally together formed with a proximal flange (562). Proximal flange (562) extends radially inwardly relative to cylindrical wall (560). An inner diameter of proximal flange (562) of knife member (540) defines an opening (544) that is configured to coaxially receive an inner core member (e.g., inner core member (312) of body member (310)). Proximal flange (562) includes an annular array of openings (546).

The annular array of openings (546) formed in knife member (540) is configured to complement the annular array of studs (556) of staple driver member (550), such that knife member (540) is fixedly secured to staple driver member (550) via studs (556) and openings (546). Particularly, FIG. 11 shows six individual studs (556) of staple driver member (550) that are disposed in six respective openings (546) of knife member (540). By way of example only, studs (556) may be heat staked to knife member (540) using techniques known in the art. Knife member (540) and staple driver member (550) may be driven distally as similarly shown in FIG. 13D regarding stapling head assembly (300). As knife member (540) translates distally, cutting edge (542) of knife member (540) cuts excess tissue that is positioned within an annular recess (e.g., annular recess (418) of anvil (400)) and the interior of knife member (540).

C. Exemplary Anvil Coupling Detection

Figure 12B:
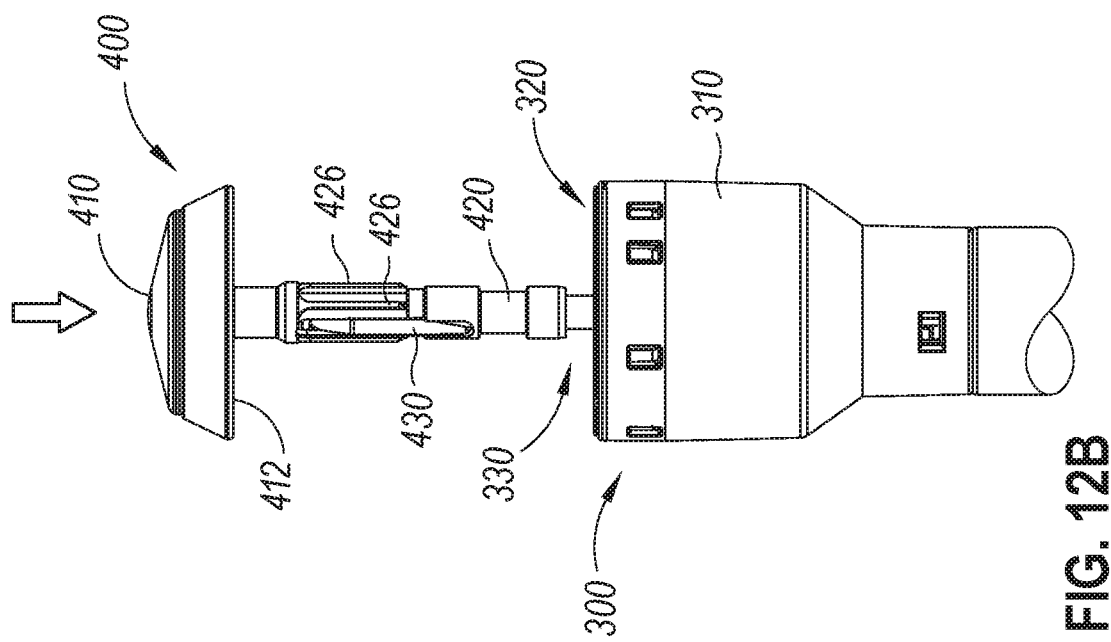
FIG. 12B shows a side elevational view of the anvil of FIG. 4 at a second longitudinal position in relation to the stapling head assembly of FIG. 7.
Figure 12A:
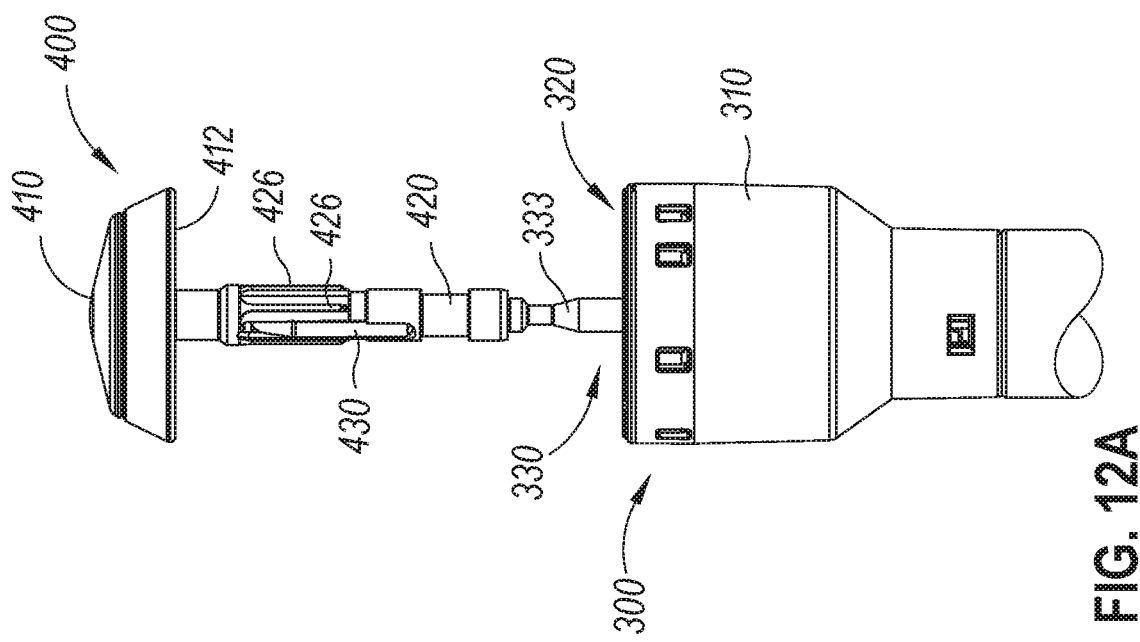
FIG. 12A shows a side elevational view of the anvil of FIG. 4 at a first longitudinal position in relation to the stapling head assembly of FIG. 7.

In some versions of instrument (10) it may desirable to provide instrument (10) with features that are configured to indicate proper and/or improper attachment of anvil (400) to trocar (330) of stapling head assembly (300). In the example shown in FIGS. 12A-12B, trocar (330) includes a colored region (333) that is longitudinally positioned at a location where colored region (333) is exposed before shank (420) is fully seated on trocar (330) (FIG. 12A); and covered when shank (420) is fully seated on trocar (330) (FIG. 12B).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Tissue Gripping Features

It may be desirable to provide a version of stapling head assembly (300) that includes features that enhance gripping of tissue during actuation of stapling head assembly (300), thereby promoting successful tissue cutting and staple deployment, without increasing the risk of damaging the patient's tissue as stapling head assembly (300) slides along the tissue during positioning of stapling head assembly (300). By way of further example only, one such deck member is shown and described in U.S. application Ser. No. 16/583,690, entitled "Circular Surgical Stapler," filed Sep. 26, 2019, issued as U.S. Pat. No. 11,123,075 on Sep. 21, 2021, the disclosure of which is incorporated by reference herein.

V. Exemplary Clamping and Firing Sequence

Figure 13A:
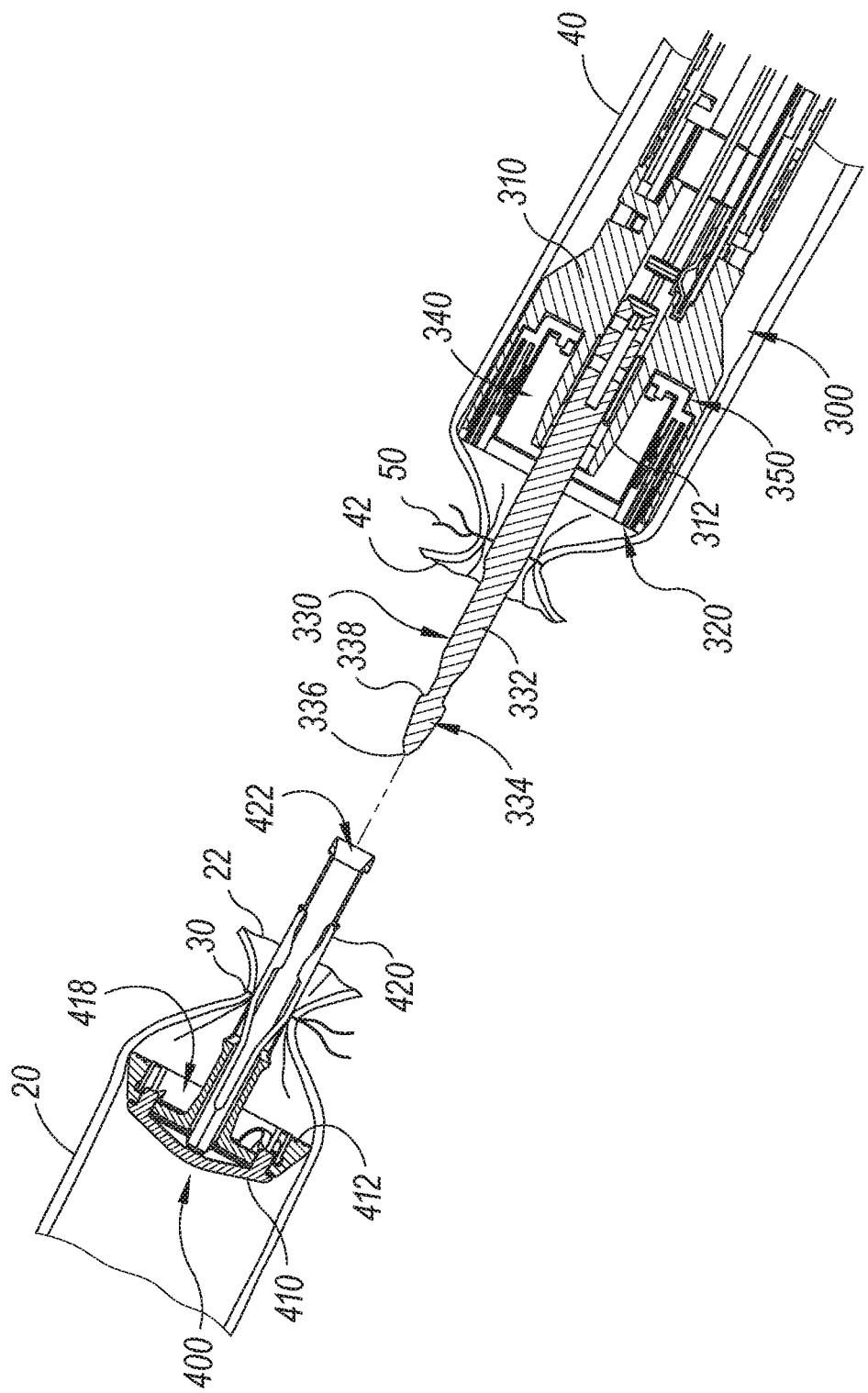
FIG. 13A depicts a cross-sectional side view of the anvil of FIG. 4 positioned within a first section of a digestive tract and the stapling head assembly of FIG. 7 positioned in a second section of the digestive tract, with the anvil separated from the stapling head assembly.

FIGS. 13A-13E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 13A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 13A-13E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 13A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 13B:
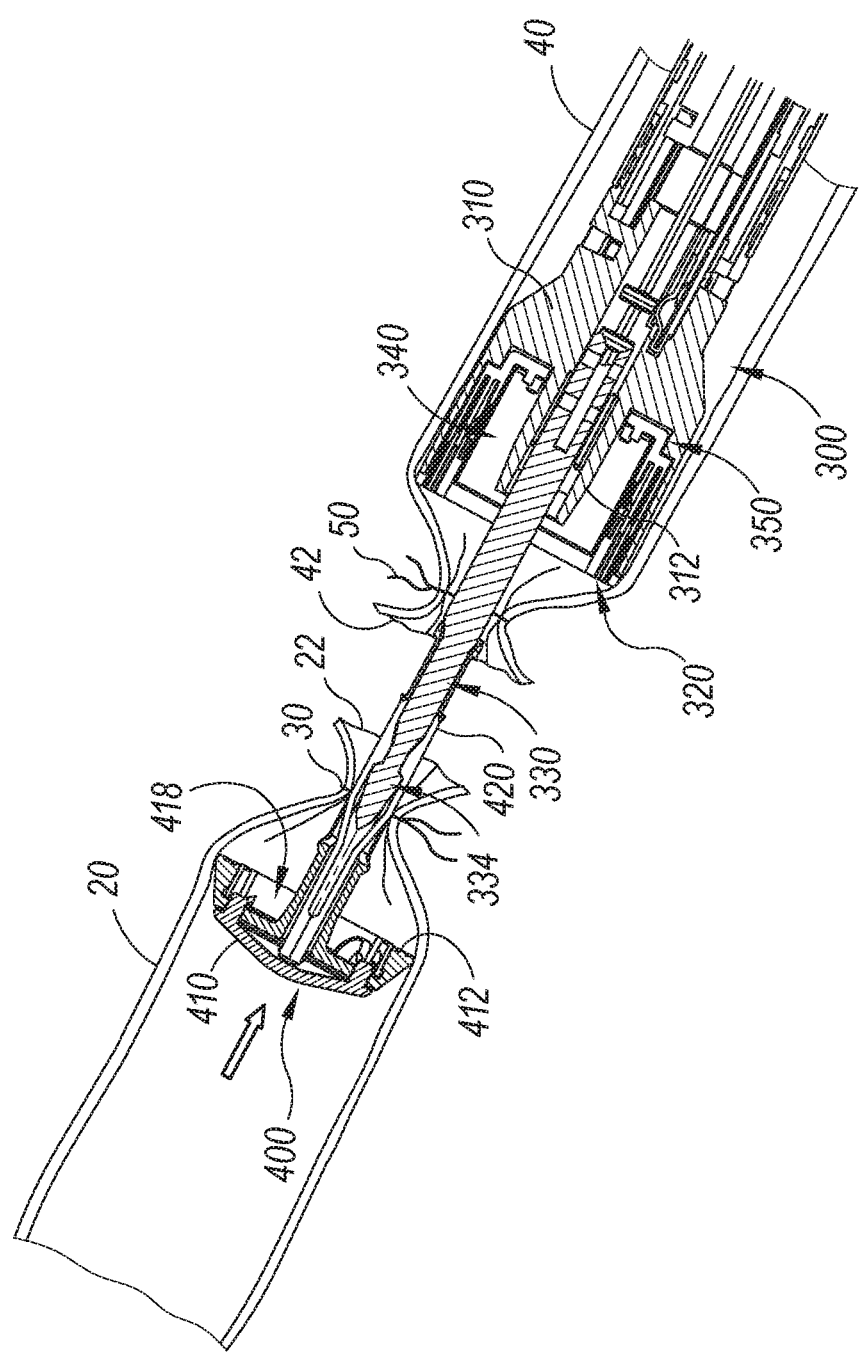
FIG. 13B depicts a cross-sectional side view of the anvil of FIG. 4 positioned within the first section of the digestive tract and the stapling head assembly of FIG. 7 positioned in the second section of the digestive tract, with the anvil secured to the stapling head assembly.
Figure 13C:
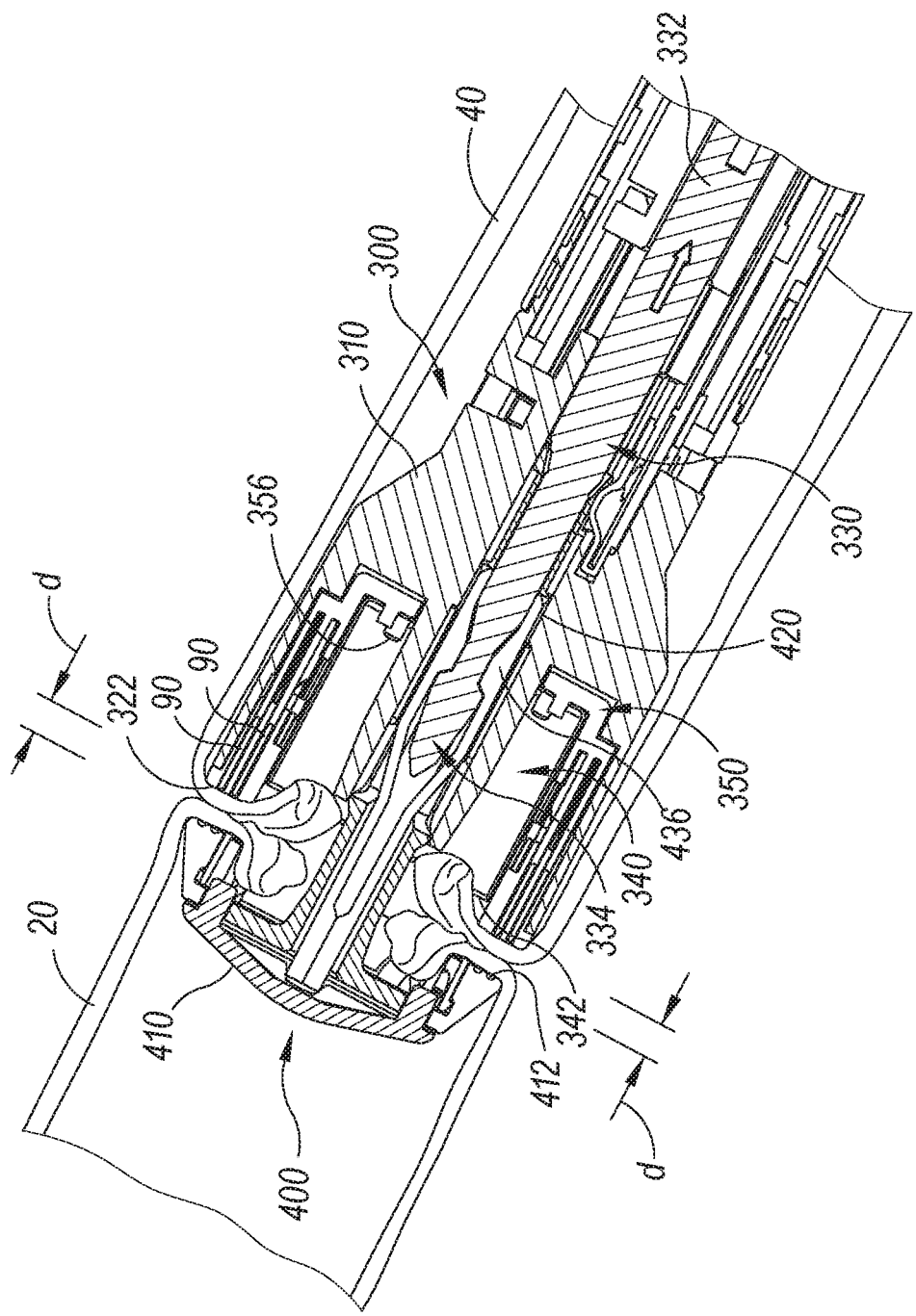
FIG. 13C depicts a cross-sectional side view of the anvil of FIG. 4 positioned within the first section of the digestive tract and the stapling head assembly of FIG. 7 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 13B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 13C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may use user feedback feature (114) to determine whether the gap distance (d) between opposing surfaces (412, 322) of anvil (400) and stapling head assembly (300) is appropriate; and make any necessary adjustments via knob (130).

Figure 13D:
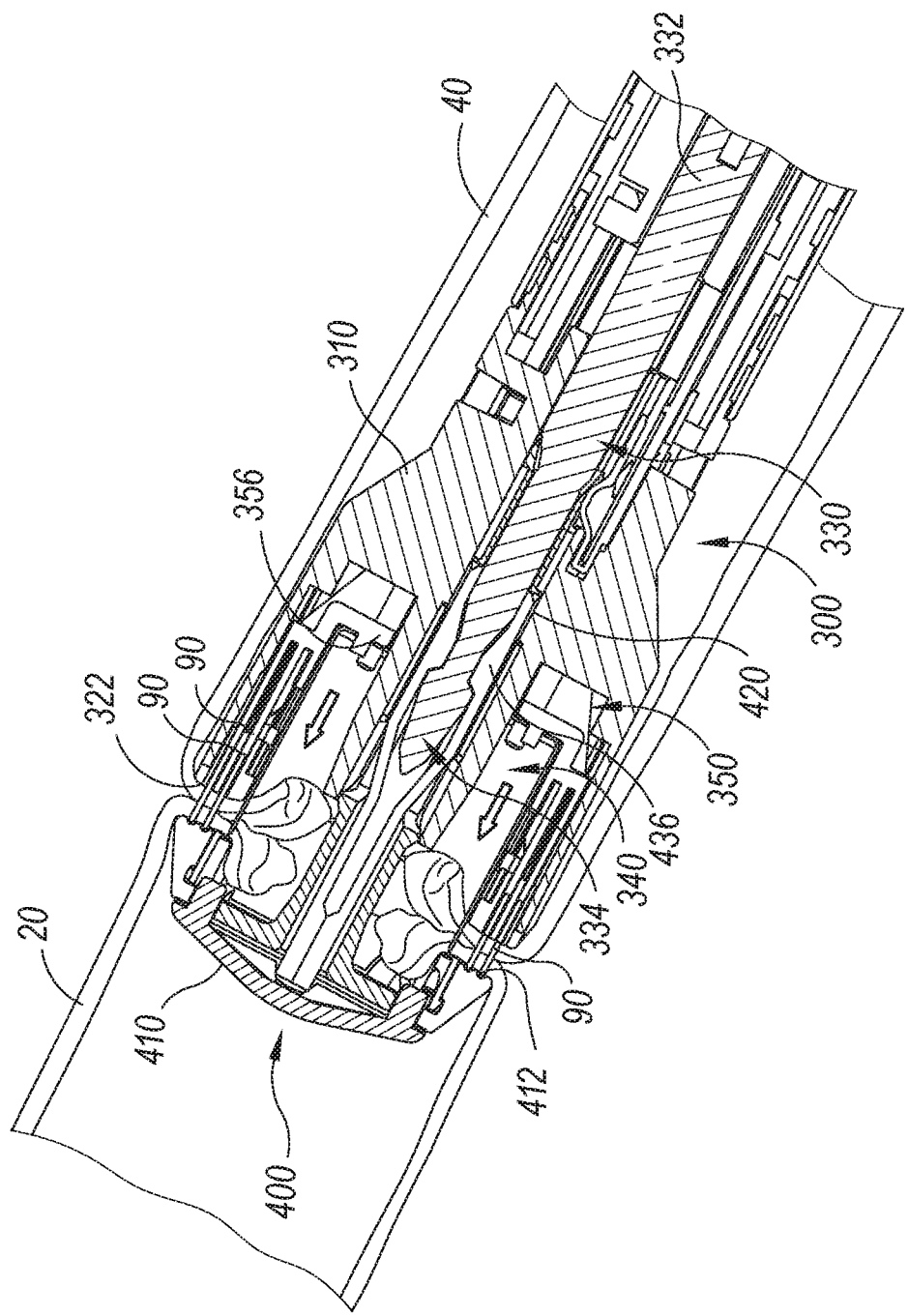
FIG. 13D depicts a cross-sectional side view of the anvil of FIG. 4 positioned within the first section of the digestive tract and the stapling head assembly of FIG. 7 positioned in the second section of the digestive tract, with the stapling head assembly actuated to sever and staple the clamped tissue.

Once the operator has appropriately set the gap distance (d) via knob (130), the operator actuates safety trigger (140) to enable actuation of firing trigger (150). The operator then actuates firing trigger (150). This actuates stapling head assembly (300) by driving knife member (340) and staple driver member (350) distally as shown in FIG. 13D. As knife member (340) translates distally, cutting edge (342) of knife member (340) cuts excess tissue that is positioned within annular recess (418) of anvil (400) and the interior of knife member (340).

As shown in FIG. 5, anvil (400) of the present example includes a breakable washer (417) within annular recess (418). This washer (417) is broken by knife member (340) when the knife member (340) completes a full distal range of motion from the position shown in FIG. 13C to the position shown in FIG. 13D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 13C to the position shown in FIG. 13D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art; or into a three-dimensional shape. In either case, the formed staples (90) secure the ends of tissue together.

After the operator has actuated stapling head assembly (300) as shown in FIG. 13D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 13E. The inner diameter of the anastomosis (70) is defined by the severed edge (60) left by knife member (340).

VI. Exemplary Alternative Knife Member Couplings

In some instances, knife members (340, 540) may be manufactured using a blank, which may be a fully annealed steel blank. The blank may be deep drawn to form proximal flange (362, 562) of knife member (340, 540). This deep drawing process may limit the material selection of knife members (340, 540) and/or may limit the range of manufacturing processes suitable for knife members (340, 540). The material selection and/or manufacturing processes may impact the mechanical properties (e.g., hardness) of the knife members (340, 540). For example, a softer material desirable for the deep drawing process may be cold-worked to obtain the desired hardness. The deep drawing process may cause cylindrical wall (360, 560) to have slight variations in the thickness of the wall. Additionally, the heat staking process used to couple knife member (340, 540) with staple driver member (350, 550) may be process dependent.

For at least these reasons, it may be desirable to couple knife member (340, 540) with staple driver member (350, 550) in a manner that increases the range of suitable materials for knife member (340, 540) to provide additional manufacturing freedom and/or provide a more uniform wall thickness of cylindrical wall (360, 560) of knife members (340, 540).

A. Indirect Knife Member Coupling

Figure 14:
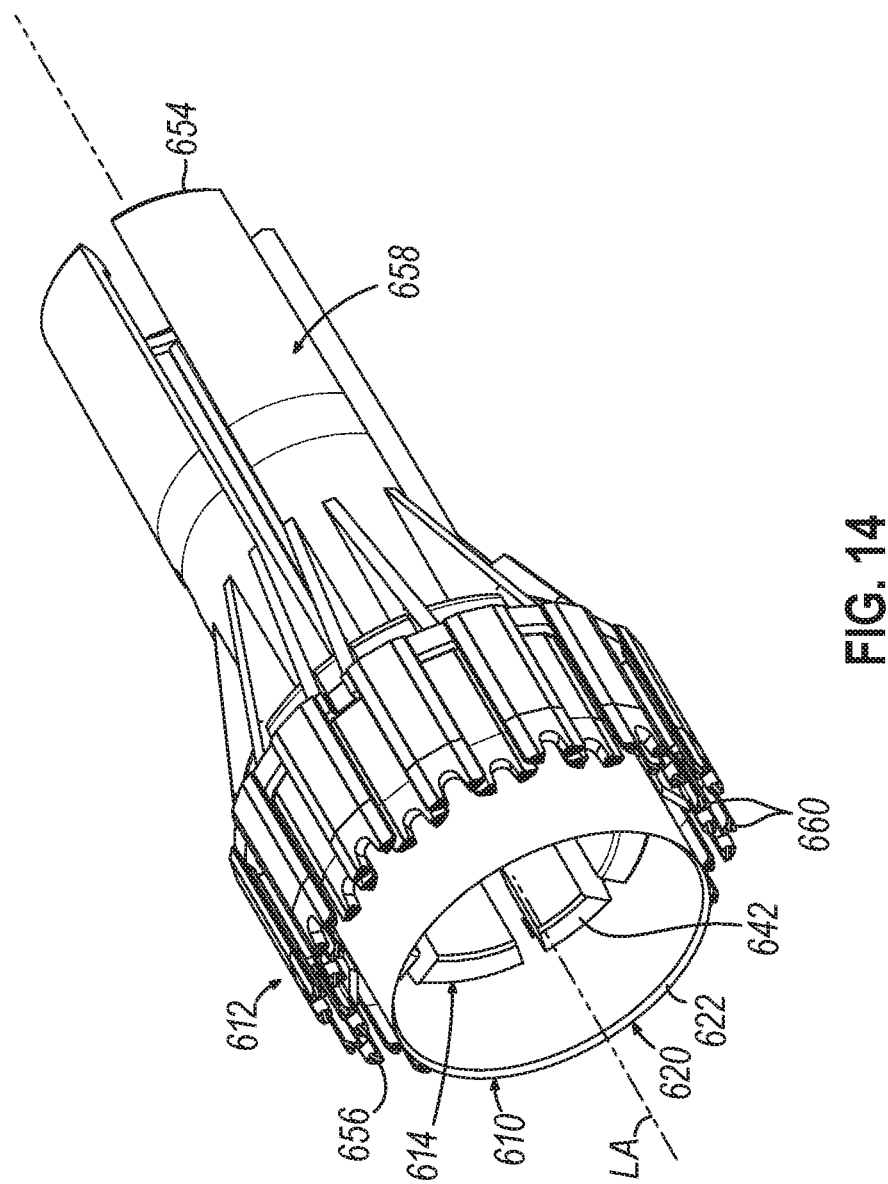
FIG. 14 depicts a perspective view of a second exemplary alternative knife member, an exemplary intermediate coupler, and a second exemplary alternative staple driver member that may be incorporated into the stapling head assembly of FIG. 7.
Figure 15:
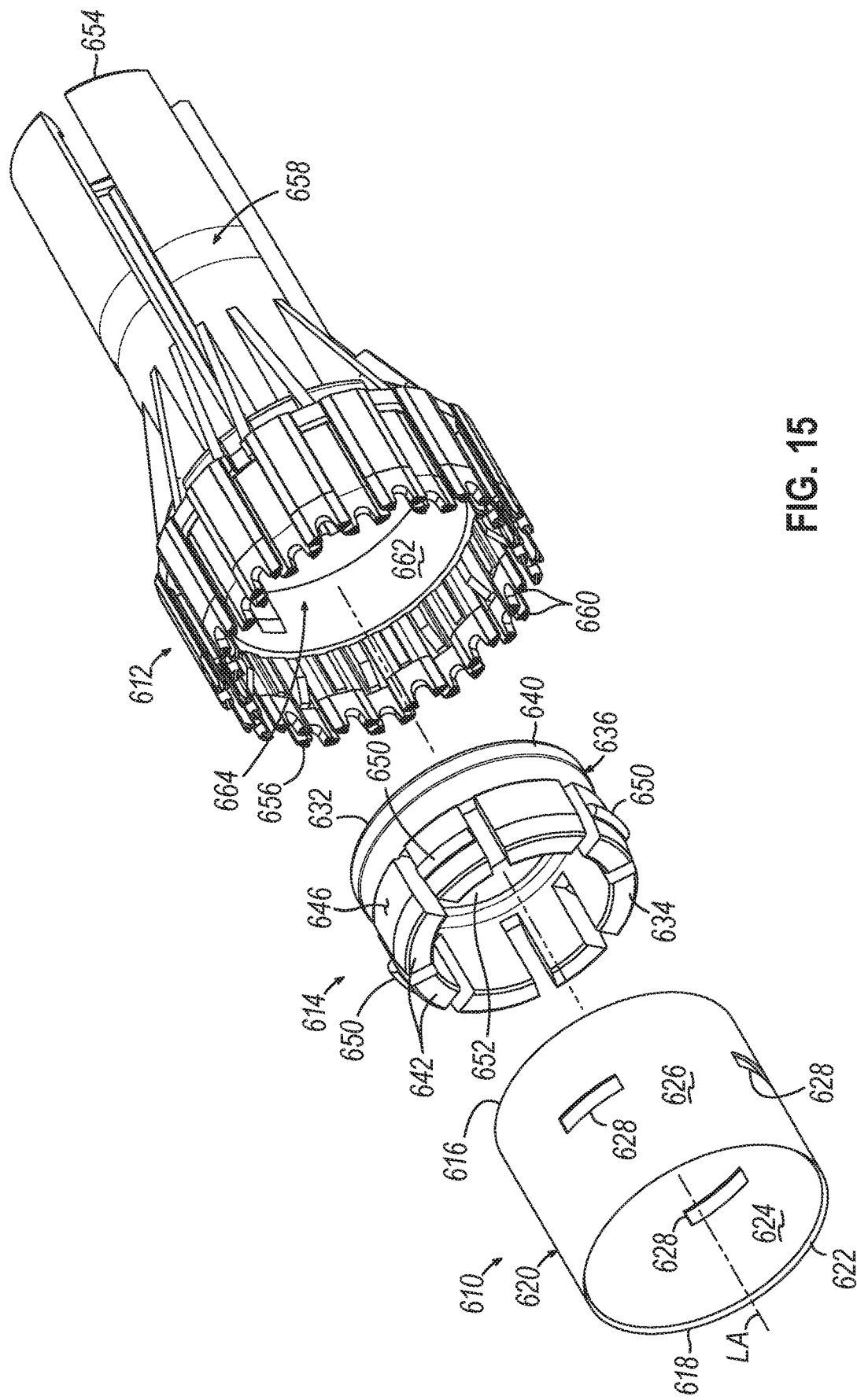
FIG. 15 depicts an exploded perspective view of the knife member, the intermediate coupler, and the staple driver member of FIG. 14.

FIGS. 14-23 show a second exemplary alternative knife member (610), a second exemplary alternative staple driver member (612), and an exemplary connector (614). Particularly, FIG. 14 shows a perspective view of knife member (610), staple driver member (612), and connector (614) and FIG. 15 shows an exploded perspective view of knife member (610), staple driver member (612), and connector (614). Knife member (610) and staple driver member (612) of this example are configured and operable like knife member (340, 540) and staple driver member (350, 550), with differences described below. Connector (614) couples with both knife member (610) and staple driver member (612), and may provide an indirect coupling between knife member (610) and staple driver member (612).

Knife member (610), staple driver member (612), and connector (614) may be incorporated into a modified version of instrument (10), which may include a body (shown as handle assembly (100)), a shaft (shown as shaft assembly (200)), and an anvil (shown as anvil (400)). For example, knife member (610), staple driver member (612), and connector (614) may be insertable into stapling head assembly (300) in place of knife member (340) and staple driver member (350). Stapling head assembly (300) may be operable to drive at least one annular array of staples (90) though tissue and may include knife member (610), staple driver member (612), connector (614), as well as inner body member (310), deck member (320), trocar (330), at least one annular array of staples (90). Stapling head assembly (300) defines a longitudinal axis (LA). Stapling head assembly (300) includes an anvil coupling feature (e.g., trocar (330)). Anvil (400) is configured to couple with trocar (330) and deform at least one annular array of staples (90) driven by staple driver member (612).

1. Second Exemplary Alternative Knife Member

Figure 16:
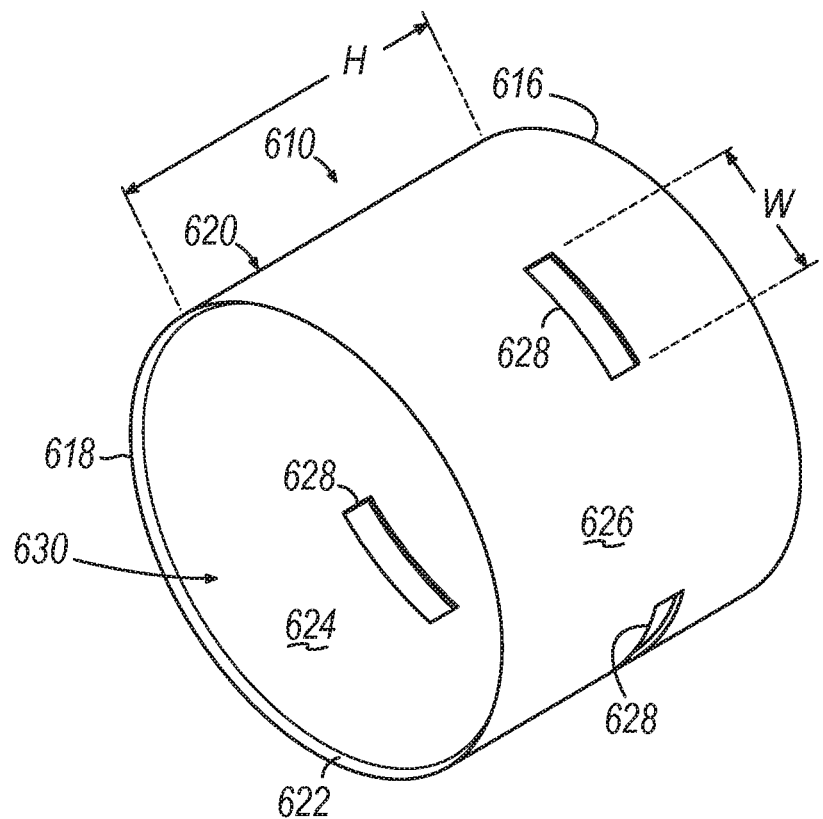
FIG. 16 depicts a perspective view of the knife member of FIG. 15.
Figure 17:
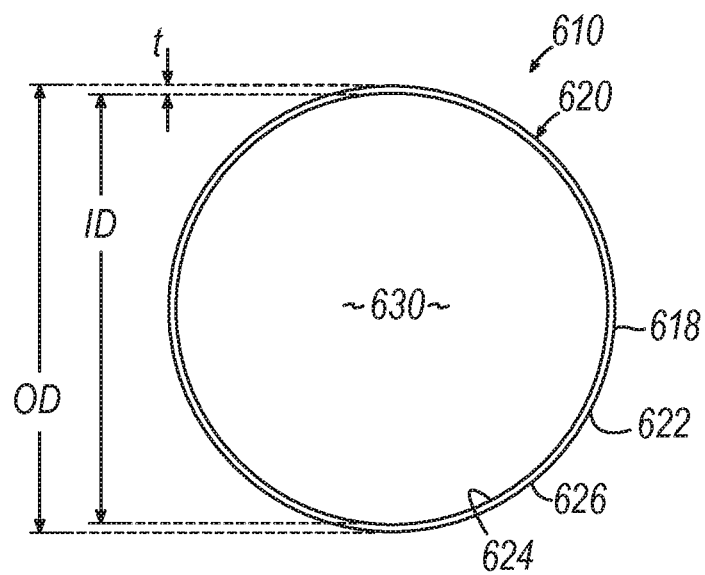
FIG. 17 depicts a top plan view of the knife member of FIG. 15.

FIGS. 16-17 show knife member (610). Particularly, FIG. 16 shows a perspective view of knife member (610) of FIG. 15, and FIG. 17 shows a top plan view of knife member (610) of FIG. 16. Knife member (610) includes a proximal end (616), a distal end (618), and a cylindrical body (620) extending between proximal and distal ends (616, 618). Distal end (618) of knife member (610) includes a circular cutting edge (622) configured to cut through tissue. Cylindrical body (620) defines inner and outer surfaces (624, 626) of knife member (610). Cylindrical body (620) extends along longitudinal axis (LA) of stapling head assembly (300). Cylindrical body (620) includes at least one coupling feature (shown as apertures (628)) that operatively couples knife member (610) with staple driver member (612). While the coupling features are shown as apertures (628), a variety of suitable coupling features are also envisioned. Additionally, while four individual radially spaced coupling features are shown, more or fewer coupler features are also envisioned, which may have the same or different spacing along knife member (610). While apertures (628) are shown as rectangular apertures that extend completely through cylindrical body (620), apertures (628) may have a variety of suitable shapes and sizes and may the same or different from one another. As shown in FIG. 16, apertures (628) have a width (W).

As shown in FIG. 17, cylindrical body (620) of knife member (610) defines a central cavity (630) that is configured to coaxially receive an inner core member (e.g., inner core member (312) of body member (310)). Similar to knife member (340, 540), knife member (610) may be coaxially positioned within staple driver member (612). As shown, cylindrical body (620) has a generally uniform thickness (t) disposed between inner and outer surfaces (624, 626). Inner surface (624) defines an inner diameter (ID) of knife member (610), and outer surface (626) defines an outer diameter (OD) of knife member (610). Unlike knife member (340, 540), proximal end (616) of knife member (610) does not include a radially inward extending proximal flange (similar to proximal flange (362, 562)). As such, knife member (610) is not shown as including annular array of openings (346, 546) disposed in proximal flanges (362, 562). Knife member (610) may be formed from a metallic material. Knife member (610) is sized such that outer diameter (OD) of knife member (610) is smaller than the diameter defined by the inner annular array of staple drivers (660) of staple driver member (610) described below. Central cavity (630) of knife member (610) is configured to coaxially receive an inner core member (e.g., inner core member (312) of body member (310)).

2. Exemplary Connector

Figure 18:
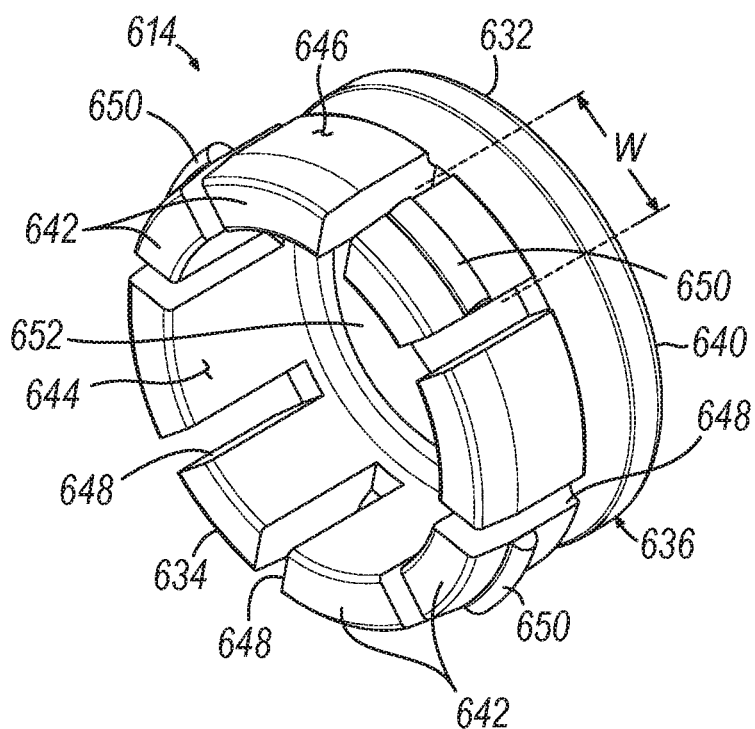
FIG. 18 depicts a perspective view of the intermediate coupler of FIG. 15.
Figure 19:
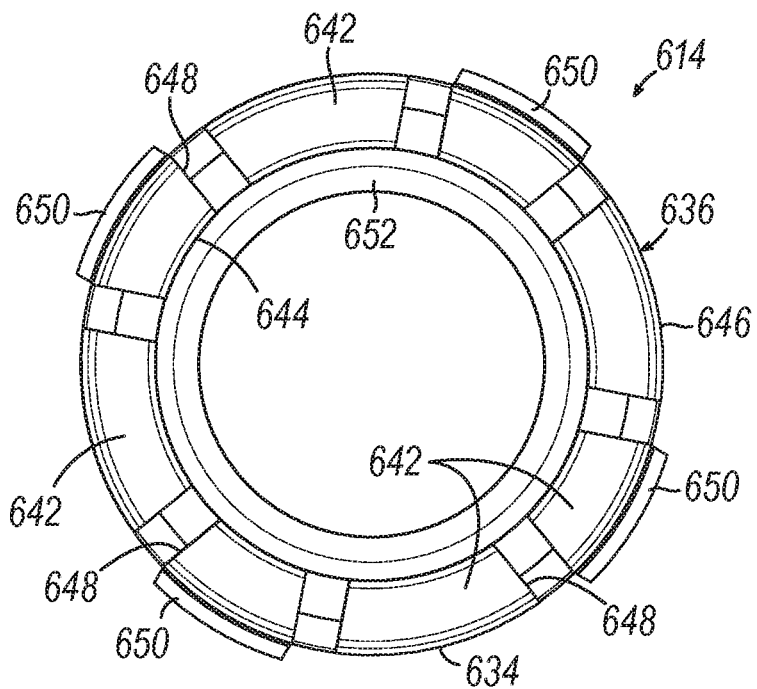
FIG. 19 depicts a top plan view of the intermediate coupler of FIG. 15.

FIGS. 18-19 show connector (614). Particularly, FIG. 18 shows a perspective view of connector (614) of FIG. 15, and FIG. 19 shows a top plan view of connector (614) of FIG. 18. As will be discussed in greater detail below with reference to FIGS. 22-23, connector (614) is configured to couple knife member (610) with staple driver member (612). For example, connector (614) may be directly coupled with both knife member (610) and staple driver member (612). As shown in FIG. 18, connector (614) includes a proximal end (632), a distal end (634), and a body (636) disposed therebetween. Proximal end (632) of connector (614) includes a planar proximal surface (638) (see FIG. 22).

Body (636) of connector (614) includes a base (640) and a plurality of arms (642) that extend distally from base (640). Body (636) defines inner and outer surfaces (644, 646). Base (640) of connector (614) may include an inwardly extending flange (652). Inwardly extending flange (652) may increase the surface area that contacts staple driver member (612) which may provide for a more robust or stronger coupling. Connector (614) may be formed from a polymeric material. Arms (642) may be flexible, such that one or more arms (642) may deflect radially inwardly to couple with knife member (610). Arms (642) may be separated by a plurality of slots (648).

Connector (614) includes at least one coupling feature (shown as projections (650)) that is lockingly engaged with at least one coupling feature of cylindrical body (620) of knife member (610). While the coupling features of connector (614) are shown as projections (650), a variety of suitable coupling features are also envisioned. Additionally, while four individual radially spaced coupling features are shown in FIG. 19, more or fewer coupling features are also envisioned having the same or different spacing. Projections (650) are shown as having a width (W) corresponding to the width (W) of apertures (628) of knife member (610). Projections (650) may extend radially outwardly from arms (642). Projections (650) extend from an outer surface (646) of body (636). Projections (650) are configured to lockingly engage with apertures (628) of cylindrical body (620) of knife member (610). While projections (650) are shown as outwardly facing rounded projections, projections (650) may have a variety of suitable shapes and sizes and may the same or different from one another. Projections (650) may be integrally formed as a unitary piece together with arms (642).

3. Second Exemplary Alternative Staple Driver Member

Figure 20:
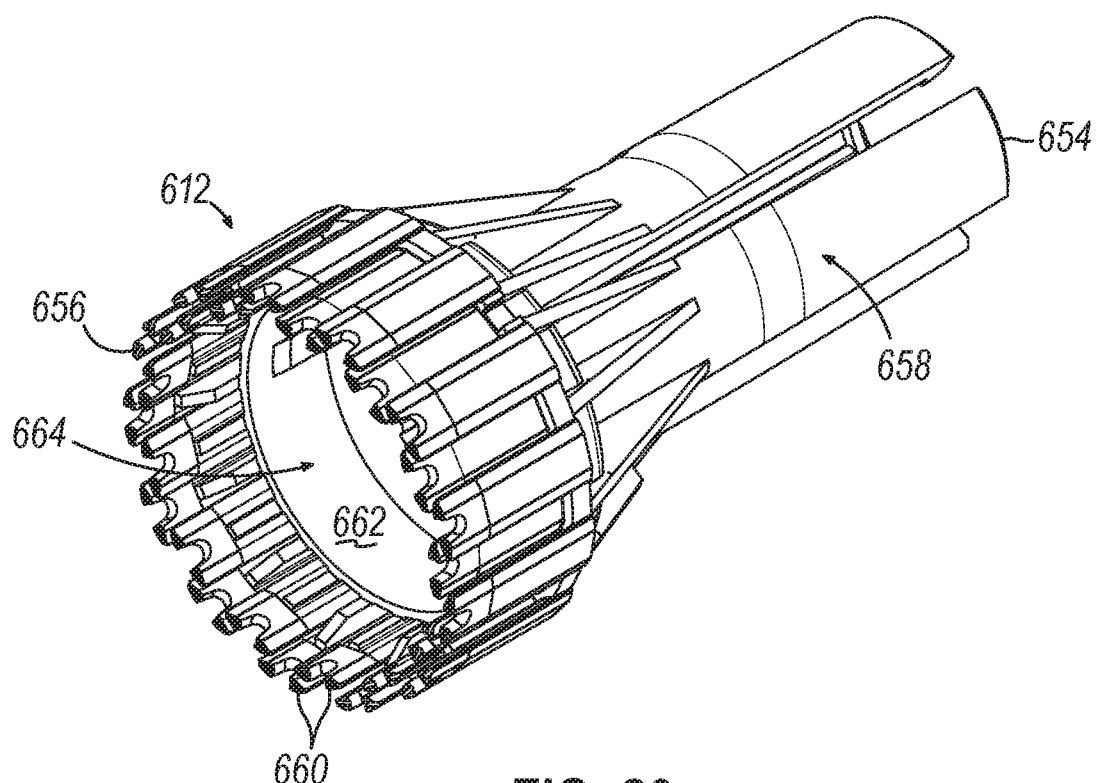
FIG. 20 depicts a perspective view of the staple driver member of FIG. 15.
Figure 21:
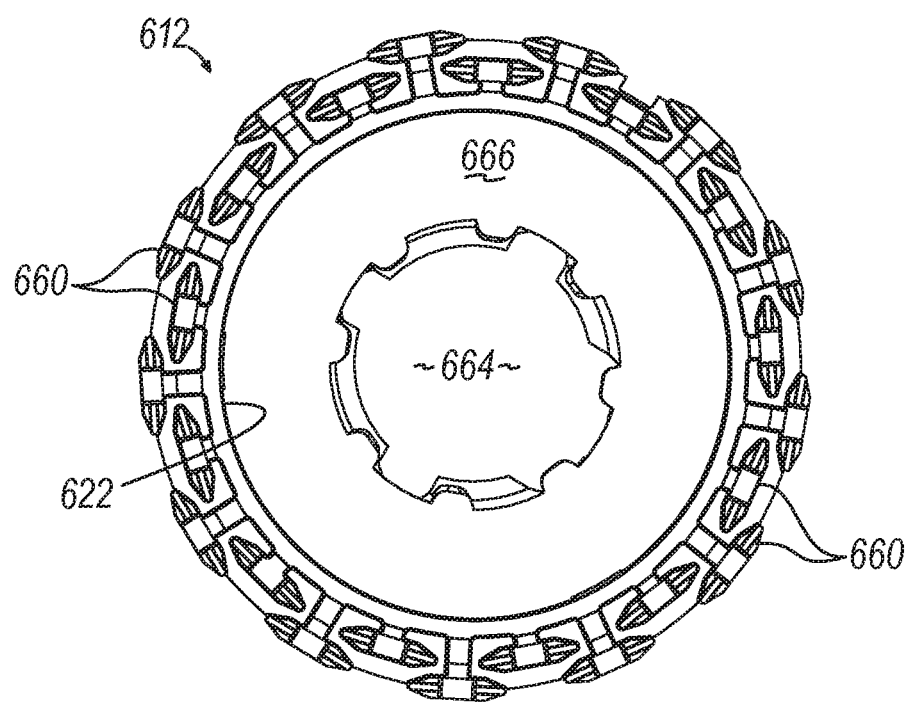
FIG. 21 depicts a top plan view of the staple driver member of FIG. 15.

FIGS. 20-21 show staple driver member (612). Particularly, FIG. 20 shows a perspective view of staple driver member (612) of FIG. 15, and FIG. 21 shows a top plan view of staple driver member (612) of FIG. 20. Similar to staple driver members (350, 550), staple driver member (612) is operable to actuate longitudinally within a body member (e.g., body member (310)) in response to activation of the motor. Staple driver member (612) includes a proximal end (654), a distal end (656), and a body (658) disposed therebetween. Body (658) includes two distally presented concentric annular arrays of staple drivers (660). Staple drivers (660) are arranged to correspond with the arrangement of staple forming pockets (similar to staple forming pockets (414)) described above. Thus, each staple driver (660) is configured to drive a corresponding staple into a corresponding staple forming pocket (414) of anvil (400) when stapling head assembly (300) is actuated.

It should be understood that the arrangement of staple drivers (660) may be modified just like the arrangement of staple forming pockets (414) as described above. Staple driver member (612) includes an inner surface (662) that defines a bore (664) that is configured to coaxially receive an inner core member (e.g., inner core member (312) of body member (310)). As shown in FIG. 21, inner surface (662) may be generally circular. Unlike staple driver member (350, 550), staple driver member (612) is not shown as including an annular array of studs (e.g., annular array of studs (356, 556)) that project distally from a distally presented surface (shown as a planar surface (666) in FIGS. 23-24) that surrounds bore (664).

Knife member (610), staple driver member (612), and connector (614) may be driven distally as similarly shown in FIG. 13D regarding stapling head assembly (300). As knife member (610) translates distally, cutting edge (622) of knife member (610) cuts excess tissue that is positioned within an annular recess (e.g., annular recess (418) of anvil (400)) and the interior of knife member (610). The inner diameter of the anastomosis is defined by the severed edge left by knife member (610). Other suitable structural relationships between knife member (610) and staple driver member (612) will be apparent to those of ordinary skill in the art in view of the teachings herein.

4. Exemplary Knife Coupling Method

Figure 22:
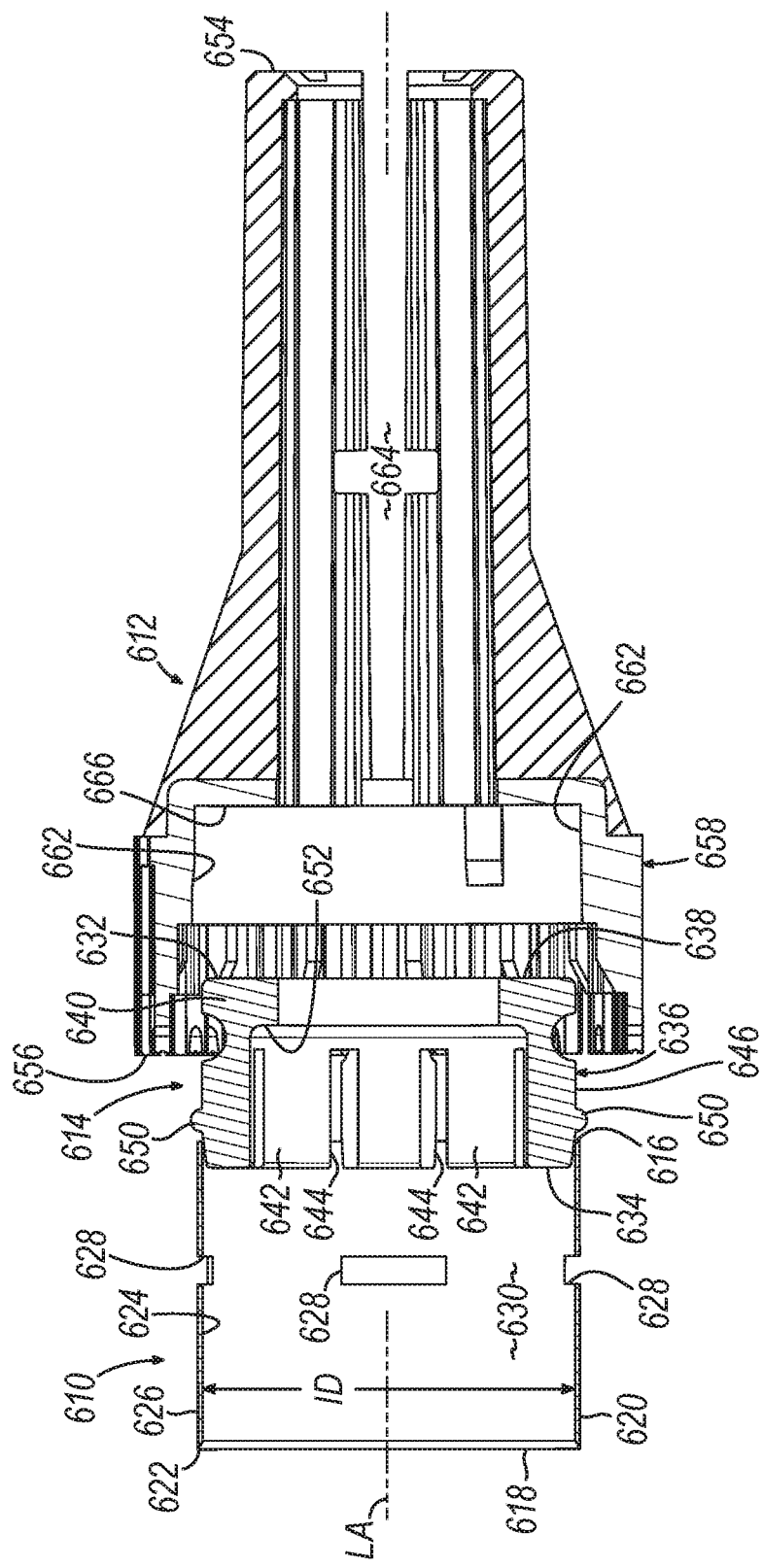
FIG. 22 depicts a cross-sectional side view of the knife member, the intermediate coupler, and the staple driver member of FIG. 14 prior to coupling.
Figure 23:
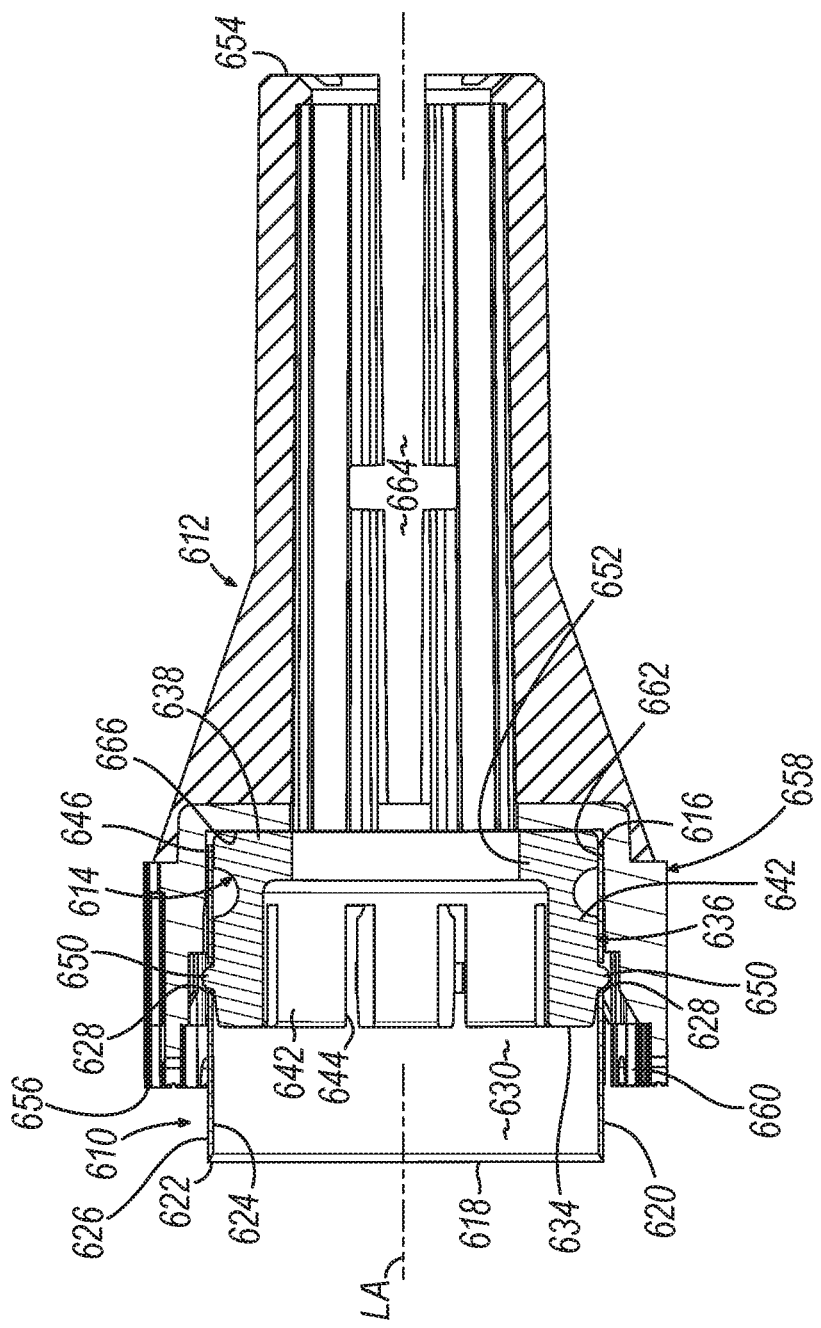
FIG. 23 depicts a cross-sectional side view of the knife member, the intermediate coupler, and the staple driver member of FIG. 14 after coupling.

A method of manufacturing is also described with reference to FIGS. 22-23. FIG. 22 shows a cross-sectional side view of knife member (610), staple driver member (612), and connector (614) of FIG. 14 prior to coupling the components together. FIG. 23 shows a cross-sectional side view of knife member (610), staple driver member (612), and connector (614) of FIG. 14 after the components are coupled together.

According to an exemplary embodiment, to form knife member (610), a long hollow tube may be cut to the desired length to produce a blank. Once the blank is formed, the blank may be centerless ground so that the blank has a uniform wall thickness. As such, knife member (610) may have greater concentricity between the inner diameter (ID) and the outer diameter (OD) relative to knife members (340, 540). The outer diameter (OD) of knife member (610) may be identical or similar to knife members (340, 540). Additionally, knife member (610) may have greater hardness, and/or be more suitable to one or more grinding processes, which is less likely to create burrs in comparison to an exemplary material (e.g., SS 305) used to form knife members (340, 540). SS 305 is an austenitic chromium-nickel stainless steel with corrosion resistance, and is suitable for severe cold forming operations. SS 305 may be better suited to deep drawing, which may be used to produce knife members (340, 540) as opposed to grinding operations, which may be used to form knife member (610). As described above, knife member (610, 710) may be formed from a metallic material. For example, knife member (610, 710) may be formed from a variety of steel alloys including, but not limited to, SS 303 and SS 304. SS 303 is an austenitic stainless steel that may allow for extensive machining operations, where the addition of sulfur may assist in breaking up turnings while reducing drag on the cutting tool. SS 304 is an austenitic stainless steel that may contain a nickel content of between approximately 8 and 10.5 percent by weight and a chromium content of between approximately 18 to 20 percent by weight. The high amounts of chromium and nickel may provide SS 304 with corrosion resistance.

It is envisioned that knife member (610) may be coupled together with connector (614) prior to or after connector (614) is coupled with staple driver member (612). For example, the method may include welding connector (614) with staple driver member (612) before or after knife member (610) is mechanically coupled with connector (614). Particularly, connector (614) may be welded to staple driver member (612), and then knife member (610) may be inserted between an inner surface (662) of staple driver member (612) and outer surface (646) of connector (614) and subsequently fixably coupled with connector (614) as described below. Alternatively, knife member (610) may be mechanically coupled with connector (614) by coupling projections (650) in apertures ((28), and then connector (614) is inserted into staple driver member (612) and fixably coupled together. As shown, planar proximal surface (638) of connector (614) may be fixably coupled together with planar surface (666) of staple driver member (612) using at least one welding process. For example, the welding process may include harmonic welding (i.e., sonic welding). However, it is also envisioned that connector (614) may be fixably coupled together with staple driver member (612) using a variety of other suitable methods (e.g., over molding).

Regarding the coupling of knife member (610) with connector (614), according to an exemplary embodiment, respective coupling features of knife member (610) and connector (614) may fixably secure knife member (610)

directly with connector (614). For example, at least one coupling feature (e.g., apertures (628)) of cylindrical body (620) of knife member (610) may couple with at least one corresponding coupling feature (e.g., projections (650)) of connector (614) to operatively couple knife member (610) with staple driver member (612). Connector (614) may be coaxially disposed within central cavity (630) of cylindrical body (620) of knife member (610).

Regarding the coupling of knife member (610) with connector (614), arms (642) of connector (614) may be flexible, such that one or more arms (642) of connector (614) may deflect radially inwardly. As shown, projections (650) of connector (614) deflect radially inwardly as knife member (610) translates relative to connector (614). To fixably secure connector (614) and staple driver member (612) together, projections (650) of connector (614) deflect back radially outwardly into corresponding apertures (628) of knife member (610). This snaps projections (650) of connector (614) into corresponding apertures (628) of knife member (610). As shown in FIG. 23, knife member (610) is indirectly coupled (i.e., not directly coupled) with staple driver member (612). However, it is also envisioned that knife member (610) may be directly coupled with staple driver member (612) as will be described below with reference to FIGS. 24-25.

Various benefits may be obtained this this coupling method, including one or more of increased sharpness of cutting edge (622) of knife member (610), a generally uniform tip radius of cutting edge (622) of knife member (610), increased hardness of knife member (610), and/or reduced variation in the height of knife member (610). Reduced variation in the height of knife member (610) may allow for a more uniform cutting force on breakable washer (417) and/or simply the manufacturing process.

B. Direct Knife Member Coupling

Figure 24:
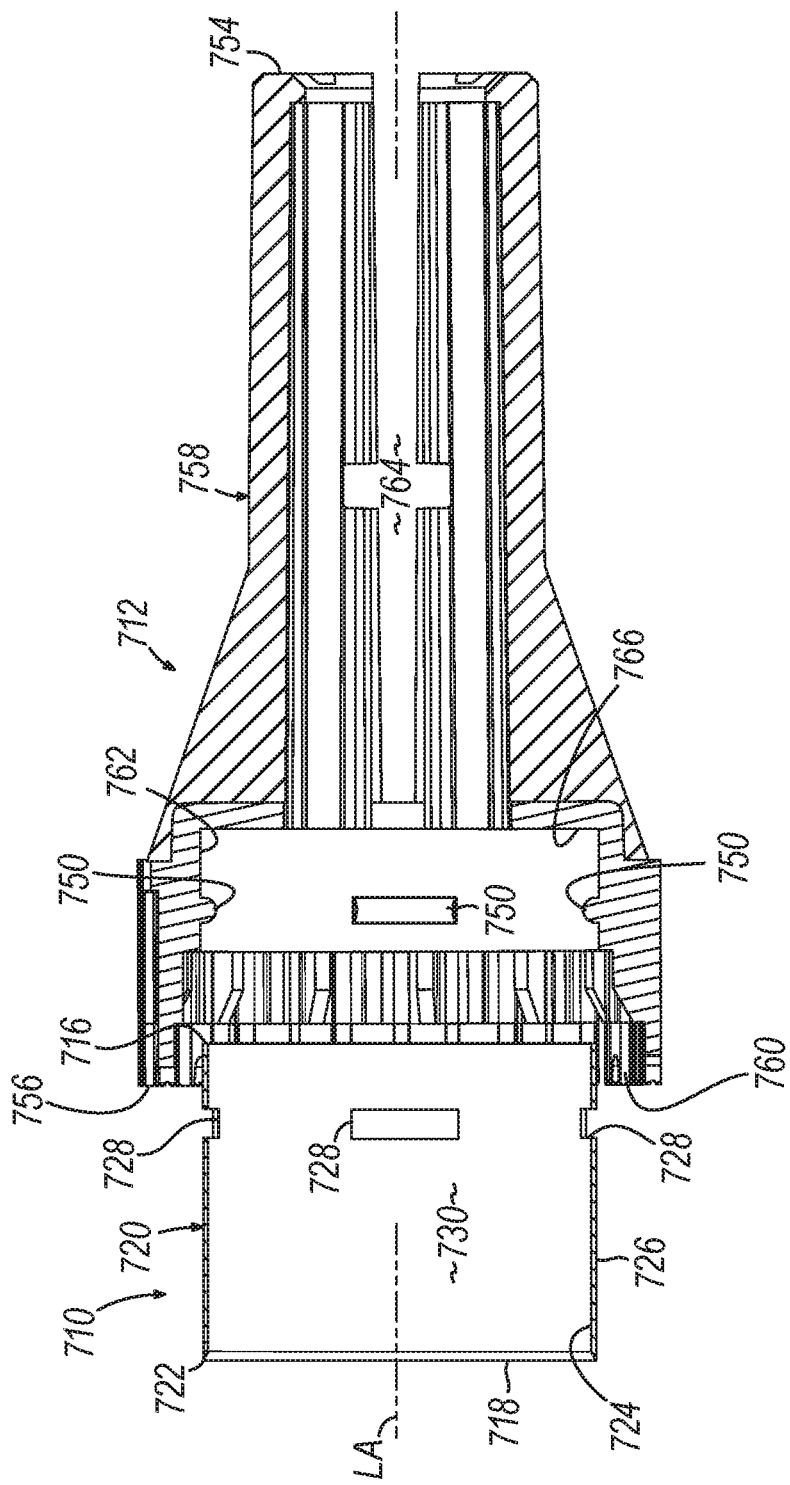
FIG. 24 depicts a cross-sectional side view of a third exemplary alternative knife member and a third exemplary alternative staple driver member that may be incorporated into the stapling head assembly of FIG. 7 prior to the knife member and the staple driver member being coupled together.
Figure 25:
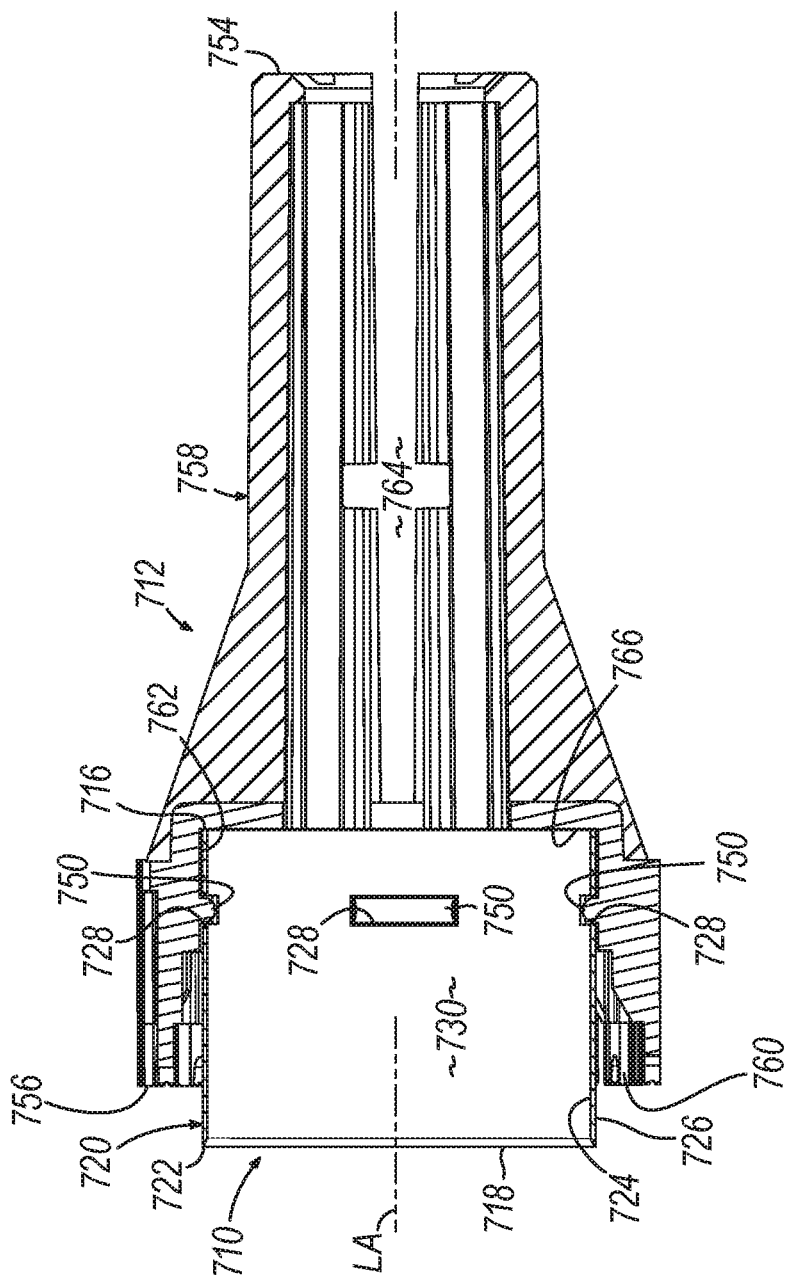
FIG. 25 depicts a cross-sectional side view of the knife member and the staple driver member of FIG. 24, but after the knife member and the staple driver member are coupled together.

FIGS. 24-25 show a third exemplary alternative knife member (710) and a third exemplary alternative staple driver member (712). FIG. 24 shows a cross-sectional side view of knife member (710), staple driver member (712) prior to coupling the components together. FIG. 25 shows a cross-sectional side view of knife member (710), staple driver member (712) after being coupled together. According to this exemplary embodiment, knife member (710) directly couples with staple driver member (712).

Knife member (710) and staple driver member (712) of this example are configured and operable like knife member (610) and staple driver member (612), with differences described below. Similar knife member (610) and staple driver member (612), knife member (710) and staple driver member (712) may be incorporated into a modified version of instrument (10), which may include a body (shown as handle assembly (100)), a shaft (shown as shaft assembly (200)), and an anvil (shown as anvil (400)). For example, knife member (710) and staple driver member (712) may be insertable into stapling head assembly (300) in place of knife member (340) and staple driver member (350).

1. Third Exemplary Alternative Knife Member

Knife member (710) is similar to knife member (610) shown and described above with reference to FIGS. 16-17 and 22-23. Knife member (710) includes a proximal end (716), a distal end (718), and a cylindrical body (720) extending between proximal and distal ends (716, 718). Distal end (718) of knife member (710) includes a circular cutting edge (722) configured to cut through tissue. Cylindrical body (720) defines inner and outer surfaces (724, 726) of knife member (710). Cylindrical body (720) extends along longitudinal axis (LA) of stapling head assembly (300). Cylindrical body (720) includes at least one coupling feature (shown as apertures (728) which may be similar to apertures (628)) that fixably couples knife member (710) with staple driver member (712). While the coupling features are shown as apertures (728), a variety of suitable coupling features are also envisioned. Similar to apertures (628), the number and spacing of apertures (728) may vary. While apertures (728) are shown as rectangular apertures that extend completely through cylindrical body (720), apertures (728) may have a variety of suitable shapes and sizes and may the same or different from one another.

As shown, cylindrical body (720) of knife member (710) defines a central cavity (730) that is configured to coaxially receive an inner core member (e.g., inner core member (312) of body member (310)). Knife member (710) may be coaxially positioned within staple driver member (712). Unlike knife member (340, 540), proximal end (716) of knife member (710) does not include a radially inward extending proximal flange (similar to proximal flange (362, 562)). As such, knife member (710) is not shown as including annular array of openings (346, 546) disposed in proximal flanges (362, 562). Knife member (710) may be formed from a metallic material. Knife member (710) is sized such that the outer diameter of knife member (710) is smaller than the diameter defined by the inner annular array of staple drivers (760) of staple driver member (710) described below. Central cavity (730) of knife member (710) is configured to coaxially receive an inner core member (e.g., inner core member (312) of body member (310)).

2. Third Exemplary Alternative Staple Driver Member

Staple driver member (712) is similar to staple driver member (612), which is shown and described above with reference to FIGS. 20-23. Similar to staple driver members (350, 550, 612), staple driver member (712) is operable to actuate longitudinally within a body member (e.g., body member (310)) in response to activation of the motor. Staple driver member (712) includes a proximal end (754), a distal end (756), and a body (758) disposed therebetween. Body (758) includes two distally presented concentric annular arrays of staple drivers (760). Staple drivers (760) are arranged to correspond with the arrangement of staple forming pockets (similar to staple forming pockets (414)) described above. Staple driver member (712) includes an inner surface (762) that defines a bore (764) that is configured to coaxially receive an inner core member (e.g., inner core member (312) of body member (310)). Unlike staple driver member (350, 550) but similar to staple driver member (612), staple driver member (712) is not shown as including an annular array of studs (e.g., annular array of studs (356, 556)) that project distally from a distally presented surface (shown as a planar surface (766) in FIGS. 24-25) that surrounds bore (764).

Unlike staple driver member (612), staple driver member (712) includes at least one coupling feature (shown as projections (750)) that is lockingly engaged with at least one coupling feature of cylindrical body (720) of knife member (710). While the coupling features of staple driver member (712) are shown as projections (750), a variety of suitable coupling features are also envisioned. Similar to projections (650), the number and spacing of projections (750) may vary. Projections (750) are configured to lockingly engage with apertures (728) of cylindrical body (720) of knife member (710). While projections (750) are shown as inwardly facing rounded projections, projections (750) may have a variety of suitable shapes and sizes and may the same or different from one another. Staple driver member (712)

may be formed from a polymeric material. Projections (750) may be integrally formed as a unitary piece together with inner surface (762).

Knife member (710) and staple driver member (712) may be driven distally as similarly shown in FIG. 13D regarding stapling head assembly (300). As knife member (710) translates distally, cutting edge (722) of knife member (710) cuts excess tissue that is positioned within an annular recess (e.g., annular recess (418) of anvil (400)) and the interior of knife member (710). Other suitable structural relationships between knife member (710) and staple driver member (712) will be apparent to those of ordinary skill in the art in view of the teachings herein.

3. Exemplary Knife Coupling Method

A method of manufacturing is also described with reference to FIGS. 24-25. According to an exemplary embodiment, respective coupling features of knife member (710) and staple driver member (712) may fixably secure knife member (710) directly with staple driver member (712). For example, at least one coupling feature (e.g., apertures (728)) of cylindrical body (720) of knife member (710) may couple with at least one corresponding coupling feature (e.g., projections (750)) of staple driver member (712) to couple knife member (710) with staple driver member (712).

Inner surface (762) of staple driver member (712) may be flexible, such that projections (750) of staple driver member (712) deflect radially outwardly as knife member (710) translates relative to staple driver member (712). To fixably secure knife member (710) and staple driver member (712) together, projections (750) of staple driver member (712) deflect back radially inwardly into corresponding apertures (728) of knife member (710). Unlike projections (650) which are outwardly facing, projections (750) are shown as being inwardly facing. This snaps projections (750) of staple driver member (712) into corresponding apertures (728) of knife member (710). As shown, there is no coupling between proximal end (716) of knife member (710) and planar surface (766) of staple driver member (712). However, it is envisioned, that planar surface (766) may be coupled with proximal end (716) in addition to the coupling provided by projections (750) of staple driver member (712) and apertures (728) of knife member (710).

VII. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft extending distally from the body; and (c) a stapling head assembly positioned at a distal end of the shaft, wherein the stapling head assembly comprises: (i) a staple driver member configured to drive a plurality of staples into tissue, and (ii) a knife member configured to cut through the tissue, wherein the knife member comprises: (A) a proximal end, (B) a distal end, and (C) a cylindrical body extending between the proximal and distal ends, wherein the cylindrical body includes at least one coupling feature that operatively couples the knife member with the staple driver member.

Example 2

The apparatus of Example 1, wherein the coupling feature of the cylindrical body is provided on a cylindrical surface of the cylindrical body.

Example 3

The apparatus of any one or more of Examples 1 through 2, wherein the stapling head assembly further comprises a connector that couples the knife member with the staple driver member.

Example 4

The apparatus of Example 3, wherein the connector is coaxially disposed within a central cavity of the cylindrical body of the knife member.

Example 5

The apparatus of any one or more of Examples 3 through 4, wherein the connector includes at least one coupling feature that is lockingly engaged with the at least one coupling feature of the cylindrical body of the knife member.

Example 6

The apparatus of any one or more of Examples 3 through 5, wherein the at least one coupling feature of the cylindrical body of the knife member includes a plurality of apertures, wherein the at least one coupling feature of connector includes a plurality of outwardly facing projections that are lockingly engaged with the plurality of apertures of the cylindrical body of the knife member.

Example 7

The apparatus of any one or more of Examples 3 through 6, wherein the connector includes a proximal end, a distal end, and a body disposed therebetween, wherein the proximal end of the connector includes a flat surface, wherein the staple driver member includes a flat surface, wherein the flat surfaces of the connector and the staple driver member are fixably coupled together.

Example 8

The apparatus of any one or more of Examples 3 through 7, wherein the connector is formed from a polymeric material.

Example 9

The apparatus of any one or more of Examples 1 through 2, wherein the staple driver member includes an inner wall, wherein the inner wall of the staple driver member includes at least one coupling feature that is lockingly engaged with the at least one coupling feature of the cylindrical body of the knife member.

Example 10

The apparatus of Example 9, wherein the at least one coupling feature of the cylindrical body of the knife member includes a plurality of apertures, wherein the at least one coupling feature of the inner wall of the staple driver member includes a plurality of inwardly facing projections that are lockingly engaged with the plurality of apertures of the cylindrical body of the knife member.

Example 11

The apparatus of any one or more of Examples 9 through 10, wherein the at least one coupling feature of the cylindrical body of the knife member is directly coupled with the at least one coupling feature of the inner wall of the staple driver member.

Example 12

The apparatus of any one or more of Examples 1 through 11, wherein the distal end of the knife member includes a circular cutting edge configured to cut through tissue.

Example 13

The apparatus of any one or more of Examples 1 through 12, wherein the stapling head assembly defines a longitudinal axis, wherein the cylindrical body of the knife member extends along the longitudinal axis.

Example 14

The apparatus of any one or more of Examples 1 through 13, wherein the stapling head assembly includes at least one annular array of staples, wherein the staple driver member is operable to drive the at least one annular array of staples though tissue.

Example 15

The apparatus of Example 14, wherein the stapling head assembly includes an anvil coupling feature, wherein the apparatus further comprises an anvil, wherein the anvil is configured to couple with the anvil coupling feature, wherein the anvil is further configured to deform the at least one annular array of staples driven by the staple driver member.

Example 16

An apparatus comprising: (a) a body; (b) a shaft extending distally from the body; and (c) a stapling head assembly positioned at a distal end of the shaft, wherein the stapling head assembly comprises: (i) a staple driver member, (ii) a knife member, wherein the knife member comprises: (A) a proximal end, (B) a distal end that includes a circular cutting edge configured to cut through tissue, and (C) a body extending between the proximal and distal ends, wherein the body includes at least one coupling feature, and (iii) a connector coupled with both the staple driver member and the knife member, wherein the connector includes at least one coupling feature lockingly engaged with the at least one coupling feature of the body of the knife member to couple the knife member with the connector.

Example 17

The apparatus of Example 16, wherein the at least one coupling feature of the body of the knife member includes a plurality of apertures, wherein the at least one coupling feature of connector includes a plurality of outwardly facing projections that are lockingly engaged with the plurality of apertures of the cylindrical body of the knife member.

Example 18

The apparatus of any one or more of Examples 16 through 17, wherein the stapling head assembly includes at least one annular array of staples, wherein the staple driver member is operable to drive the at least one annular array of staples though the tissue.

Example 19

A method of manufacturing a surgical stapler, wherein the surgical stapler includes a body, a shaft extending distally from the body, and a stapling head assembly positioned at a distal end of the shaft, wherein the stapling head assembly includes a staple driver member and a knife member, wherein the knife member includes a proximal end, a distal end, and a cylindrical body extending therebetween, the method comprising: (a) coupling at least one coupling feature of the cylindrical body of the knife member with at least one corresponding coupling feature of one of the staple driver member or a connector to thereby operatively couple the knife member with the staple driver member.

Example 20

The method of Example 19, further comprising harmonically welding the connector with the staple driver member.

VIII. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may also be readily combined with one or more teachings of U.S. Pub. No. 2017/0258471, entitled "Methods and Systems for Performing Circular Stapling," published Sep. 14, 2017, issued as U.S. Pat. No. 10,709,452 on Jul. 14, 2020, the disclosure of which is incorporated by reference herein; U.S. Pub. No. 2015/0083772, entitled "Surgical Stapler with Rotary Cam Drive and Return," published Mar. 26, 2015, now abandoned, the disclosure of which is incorporated by reference herein; U.S. Pat. No. 9,936,949, entitled "Surgical Stapling Instrument with Drive Assembly Having Toggle Features," issued Apr. 10, 2018, the disclosure of which is incorporated by reference herein; U.S. Pat. No. 9,907,552, entitled "Control Features for Motorized Surgical Stapling Instrument," issued Mar. 6, 2018, the disclosure of which is incorporated by reference herein; U.S. Pat. No. 9,713,469, entitled "Surgical Stapler with Rotary Cam Drive," issued Jul. 25, 2017, the disclosure of which is incorporated by reference herein; U.S. Pat. No. 10,226,253, entitled "Firing Assembly for Circular Stapler," issued Mar. 12, 2019, the disclosure of which is incorporated by reference herein; U.S. Pat. No. 10,478,189, entitled "Method of Applying an Annular Array of Staples to Tissue," issued Nov. 19, 2019, the disclosure of which is incorporated by reference herein. Various suitable ways in which the teachings herein may be combined with the teachings of the above-referenced patents, publications, and patent applications will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). As another merely illustrative example, the various teachings herein may be readily applied to a motorized electrosurgical device. For instance, various teachings herein may be readily combined with various teachings of U.S. Pat. No. 9,161,803, entitled "Motor Driven Electrosurgical Device with Mechanical and Electrical Feedback," issued Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a body;
(b) a shaft extending distally from the body; and
(c) a stapling head assembly positioned at a distal end of the shaft, wherein the stapling head assembly comprises:
(i) at least one coupling feature;
(ii) a staple driver member configured to drive a plurality of staples into tissue, and
(iii) a knife member configured to cut through the tissue, wherein the knife member comprises:
(A) a proximal end,
(B) a distal end, and
(C) a cylindrical body extending between the proximal and distal ends, wherein the cylindrical body includes at least one aperture, wherein the at least one coupling feature extends at least partially within the at least one aperture to operatively couple the knife member with the staple driver member, wherein the at least one aperture is spaced apart from the proximal end.

2. The apparatus of claim 1, wherein the stapling head assembly further comprises a connector that couples the knife member with the staple driver member.

3. The apparatus of claim 2, wherein the connector is coaxially disposed within a central cavity of the cylindrical body of the knife member.

4. The apparatus of claim 2, wherein the connector includes the at least one coupling feature that is lockingly engaged with the at least one aperture of the cylindrical body of the knife member.

5. The apparatus of claim 2, wherein the at least one aperture of the cylindrical body of the knife member includes a plurality of apertures, wherein the connector includes the at least one coupling feature, wherein the at least one coupling feature of the connector includes a plurality of outwardly facing projections that are lockingly engaged with the plurality of apertures of the cylindrical body of the knife member.

6. The apparatus of claim 2, wherein the connector includes a proximal end, a distal end, and a body disposed therebetween, wherein the proximal end of the connector includes a flat surface, wherein the staple driver member includes a flat surface, wherein the flat surfaces of the connector and the staple driver member are fixably coupled together.

7. The apparatus of claim 1, wherein the staple driver member includes an inner wall, wherein the inner wall of the staple driver member includes the at least one coupling feature that is lockingly engaged with the at least one aperture of the cylindrical body of the knife member.

8. The apparatus of claim 7, wherein the at least one aperture of the cylindrical body of the knife member includes a plurality of apertures, wherein the at least one coupling feature of the inner wall of the staple driver member includes a plurality of inwardly facing projections that are lockingly engaged with the plurality of apertures of the cylindrical body of the knife member.

9. The apparatus of claim 7, wherein the at least one aperture of the cylindrical body of the knife member is directly coupled with the at least one coupling feature of the inner wall of the staple driver member.

10. The apparatus of claim 1, wherein the distal end of the knife member includes a circular cutting edge configured to cut through tissue.

11. The apparatus of claim 1, wherein the stapling head assembly includes at least one annular array of staples, wherein the staple driver member is operable to drive the at least one annular array of staples though tissue.

12. The apparatus of claim 1, wherein the proximal end of the knife member does not include a radially inward extending proximal flange.

13. The apparatus of claim 1, wherein the proximal end is not in direct contact with the staple driver member.

14. An apparatus comprising:
 (a) a body;
 (b) a shaft extending distally from the body; and
 (c) a stapling head assembly positioned at a distal end of the shaft, wherein the stapling head assembly comprises:
  (i) a staple driver member,
  (ii) a knife member, wherein the knife member comprises:
   (A) a proximal end,
   (B) a distal end that includes a circular cutting edge configured to cut through tissue, and
   (C) an intermediate body extending between the proximal and distal ends, wherein the intermediate body includes at least one aperture disposed entirely between the proximal and distal ends, and
  (iii) a connector coupled with both the staple driver member and the knife member, wherein the connector includes at least one arm configured to deflect radially inwards to receive the knife member, wherein the arm includes an outwardly facing projection lockingly engaged with the at least one aperture of the intermediate body of the knife member to couple the knife member with the connector.

15. The apparatus of claim 14, wherein the at least one aperture of the intermediate body of the knife member includes a plurality of apertures, wherein the at least one arm includes a plurality of arms with the outwardly facing projection including a plurality of outwardly facing projections that are lockingly engaged with the plurality of apertures of the intermediate body of the knife member.

16. The apparatus of claim 14, wherein the stapling head assembly includes at least one annular array of staples, wherein the staple driver member is operable to drive the at least one annular array of staples though the tissue.

17. The apparatus of claim 14, wherein the proximal end of the knife member does not include a radially inward extending proximal flange.

18. A method of manufacturing a surgical stapler, wherein the surgical stapler includes a body, a shaft extending distally from the body, and a stapling head assembly positioned at a distal end of the shaft, wherein the stapling head assembly includes a staple driver member and a knife member, wherein the knife member includes a proximal end, a distal end, and a cylindrical body extending therebetween, the method comprising:
 (a) forming at least one aperture in the cylindrical body of the knife member at a non-zero distance from the proximal end; and
 (b) inserting at least one corresponding coupling feature of one of the staple driver member or a connector into the at least one aperture of the cylindrical body of the knife member to thereby operatively couple the knife member with the staple driver member.

19. The method of claim 18, further comprising harmonically welding the connector with the staple driver member before or after the act of inserting.

20. The method of claim 18, wherein forming the at least one aperture further comprises removing material from the cylindrical body of the knife member to form the at least one aperture.

* * * * *